United States Patent [19]

Siegel et al.

[11] Patent Number: 5,365,426
[45] Date of Patent: Nov. 15, 1994

[54] ADVANCED SIGNAL PROCESSING METHODOLOGY FOR THE DETECTION, LOCALIZATION AND QUANTIFICATION OF ACUTE MYOCARDIAL ISCHEMIA

[75] Inventors: John H. Siegel, Baltimore, Md.; Chrysostomos L. Nikias, Needham, Mass.

[73] Assignee: The University of Maryland, Baltimore, Md.

[21] Appl. No.: 586,108

[22] Filed: Sep. 21, 1990

Related U.S. Application Data

[63] Continuation-in-part of Ser. No. 25,896, Mar. 13, 1987, Pat. No. 4,974,162.

[51] Int. Cl.$^5$ .......................... G06F 15/00; A61B 5/04
[52] U.S. Cl. .............................. 364/413.06; 128/702
[58] Field of Search ................... 364/413.06; 128/702, 128/703, 902

[56] References Cited

U.S. PATENT DOCUMENTS

4,930,075  5/1990  Kortas ............................. 364/413.06
4,989,610  2/1991  Patton et al. .................... 264/413.06

OTHER PUBLICATIONS

Nikias et al., "Frequency-wave number inverse model for electrocardiography", Proc. 8th Annual Int. Conf. IEEE Engin in medicine and biology, pp. 307-310, CH2368-Sep. 1986.

Siegel et al., "Epicardial Electrical Activation Analyzed via Frequency-Wave Number Spectrum Estimation for the Characterization of Arrthythmiagenic States", J. electrocardial, vol. 20(5), 1987, 329-351, Proc. 12th Northeast Bioeng. Conf., p. 199, Yale University, Mar. 1986.

Nikias et al., "Spetrum estimation for the analysis of array ECG." Proc. 7th annual Int. Conf. IEEE Engin. in Medicine and Biology, Chicago, Sep. 1985.

Rush et al., "Multiple Peaks from a Single Dipole in a Homogeneous Torso Model", Body Surface Mapping of Cardiac Fields, Adv. Cardiol., vol. 10, pp. 89-93, 1974.

Rush "Effects of Dipole Separation on Surface Potentials", Body Surface Mapping of Cardiac Fields, Adv. Cardiol., vol. 10, pp. 240-246, 1974.

Rush et al., "A New Normalized Image . . . ", Body Surface Mapping of Cardiac Fields, Adv. Cardiol., vol. 10, pp. 64-68, 1974.

Enderle, et al., "Computer interpretation of ECG and vectorcadiograms", Advances in Cardiol. vol. 16, pp. 194-202, 1976.

Jain, et al., "The stability of decision theoretic electrocardiographic classifiers based on the use of disoretized feature", Comp., Biomed. Res., vol. 13, p. 695, 1980.

Tompkins et al., "Body Surface Mapping by Equivalent Generator Techniques", Body Surface Mapping of Cardiac Fields, Adv. Cardiol., vol. 10, pp. 161-166, 1974.

Durrer et al., "Total Excitation of the Isolated Human Heart", Circulation, vol. 41, pp. 899-912, Jun. 1970.

Franz et al., "Localization of regional myocardial ischemia by recording of monophonic action potentials", Circulation, vol. 69, pp. 593-604, Mar. 1984.

Roberge, "Some emerging issues in electrocardiology", pp. 59-61, IEEE Press No. 86 CH2369-7, 1986.

Kornreich et al., "Effective extraction of Diagnostic ECG waveform infor. using orthonormal Basis functions derived from body surface potentials maps." Journ. electrocardiol.; vol. 18(4), pp. 341-350, 1985.

(List continued on next page.)

*Primary Examiner*—Robert A. Weinhardt
*Assistant Examiner*—X. M. Chung-Trans
*Attorney, Agent, or Firm*—Sughrue, Mion, Zinn, Macpeack & Seas

[57] ABSTRACT

Monopolar ECG signals are converted into the multichannel spectrum and autocorrelation domains, and different decision variables are identified from the autospectra. Statistically validated threshold levels are used for comparison with the decision variables to determine the probability of normal and ischemic conditions.

14 Claims, 28 Drawing Sheets

OTHER PUBLICATIONS

Nichols et al., "Frequency Content of the ECG Spatial Features and Effects of Myocardial infarction"., *J. electrocardiol.* vol. 18(2), pp. 185–194, 1985.

Nikias et al., "The Zero delay wave number spectrum estimation for the Analysis of Array ECG Signals–An Alternative to isopotential mapping", IEEE Trans. Biomed. Engin., vol. BME 33, No. 4 pp. 435–452, Apr. 1986.

Jenins, Janice M., "Automated Electrocardiography and Arrhythmia Monitoring", *Progress in Cardiovacular Disease*, vol. XXV, No. 5, Mar./Apr., 1983–ppl 367–408.

Laxter, Cary et al, "The Use of Unipolar Epicardial QRS Potentials to Estimate Myocardial Infraction", *IEEE Transactions on Biomedical Engineering*, vol. BME-32, No. 1, Jan. 1985, pp. 64–67.

Helppi, Reino R. et al, "Suggested Minimal Performance Requirements and Methods of Performance Evaluation of Computer ECG Analysis Programs", *C.M.A. Journal*, May 19, 1973/vol. 108, pp. 1251–1259.

Claydon, Frank J. et al "Classification of Heart Tissue from Bipolar and Unipolar Intramural Potentials", *1985 IEEE*, pp. 513–520.

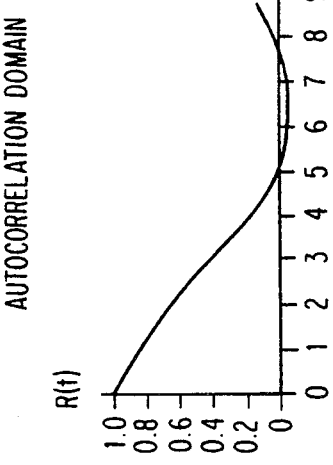
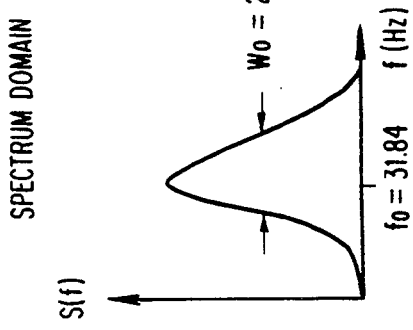
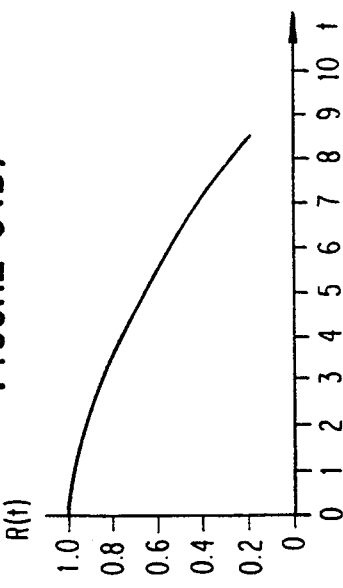
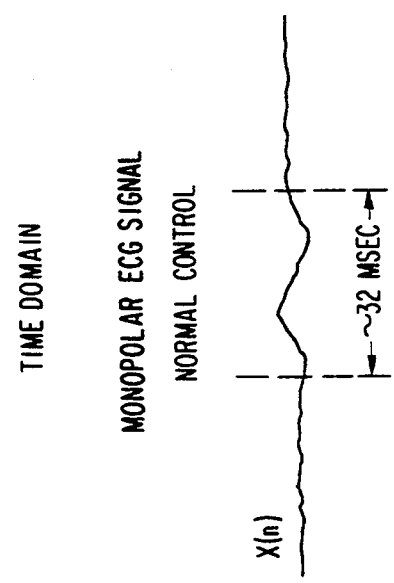
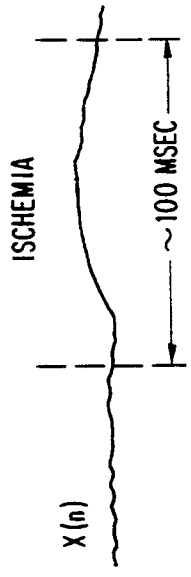

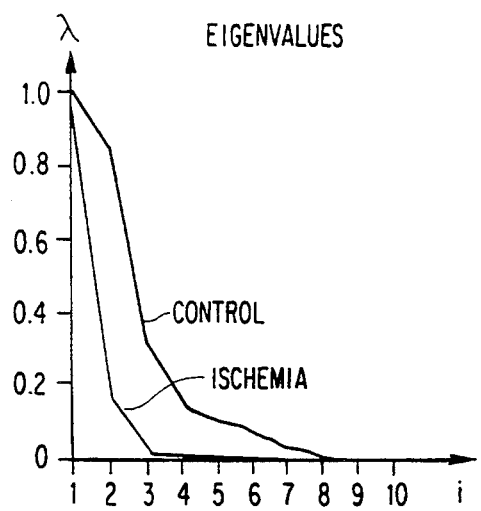
FIGURE 4(A)
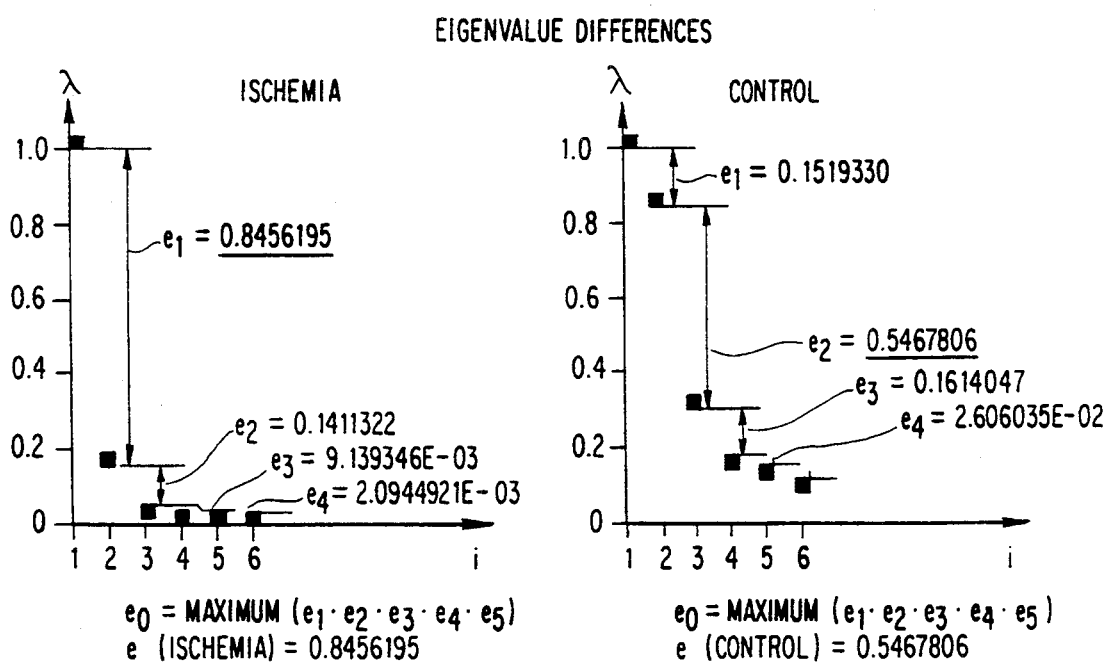
FIGURE 4(B)  FIGURE 4(C)

↓ 4

Estimate Autocorrelation (AC) Sequence

$$R(m) = \frac{1}{n} \sum_{n=0}^{N-1-m} X(n) X(n+m)$$

$m = 0, 1, \ldots, M$

Usually M can take any value between 6-10

—11

16
18

Form AC Matrix

$$\underline{R} = \begin{bmatrix} R(0) & R(1) & \cdots & R(M) \\ R(1) & R(0) & \cdots & R(M-1) \\ \cdot & \cdot & & \cdot \\ \cdot & \cdot & & \cdot \\ \cdot & \cdot & & \cdot \\ R(M) & R(M-1) & \cdots & R(0) \end{bmatrix}$$ Toeplitz and Symmetrix $(M+1) \times (M+1)$

—12

Compute eigenvalues of $\underline{R}$

$\lambda_0 \geq \lambda_1 \geq \lambda_2 \geq \lambda_3 \geq \lambda \ldots \ldots \geq \lambda_M \geq 0$ IF $|\lambda_i|$ $10^{-5}$, THEN PUT $\lambda_i = 0$

Compute eigenvalue differences

$$e_i = \left| \frac{\lambda_i - \lambda_{i-1}}{\lambda_0} \right|$$

$i = 1, 2, \ldots, M$

— 14

Compute $e_0$

$$e_0 = \text{MAX}\left[e_1, e_2, \ldots, e_M\right]$$

Fopt = 12.0      F

Wopt = 22.0      W

Eopt = 0.72      E

DECISION VARIABLES

| SENSOR # | FOPT | WOPT | EOPT |
|---|---|---|---|
| 12 | 31.250 | 24.414 | 0.582 |
| 11 | 30.273 | 24.414 | 0.519 |
| 10 | 28.320 | 24.414 | 0.570 |
| 9 | 17.578 | 23.438 | 0.494 |
| 8 | 33.203 | 28.320 | 0.480 |
| 7 | 30.273 | 25.391 | 0.493 |
| 6 | 27.344 | 24.414 | 0.581 |
| 5 | 23.438 | 21.484 | 0.600 |
| 4 | 29.297 | 27.344 | 0.607 |
| 3 | 27.344 | 26.367 | 0.651 |
| 2 | 24.414 | 20.508 | 0.521 |
| 1 | 22.461 | 24.414 | 0.707 |

FIGURE 23(C)

DECISION VARIABLES

| SENSOR # | FOPT | WOPT | EOPT |
|---|---|---|---|
| 12 | 34.180 | 23.438 | 0.491 |
| 11 | 33.203 | 23.438 | 0.510 |
| 10 | 29.297 | 27.344 | 0.689 |
| 9 | 14.648 | 23.438 | 0.524 |
| 8 | 31.250 | 28.320 | 0.427 |
| 7 | 8.789 | 11.719 | 0.817 |
| 6 | 8.789 | 11.719 | 0.846 |
| 5 | 9.766 | 12.695 | 0.816 |
| 4 | 8.789 | 11.719 | 0.877 |
| 3 | 8.789 | 11.719 | 0.878 |
| 2 | 8.789 | 11.719 | 0.900 |
| 1 | 9.766 | 12.695 | 0.859 |

FIGURE 24(C)

ADVANCED SIGNAL PROCESSING METHODOLOGY FOR THE DETECTION, LOCALIZATION AND QUANTIFICATION OF ACUTE MYOCARDIAL ISCHEMIA

This is a continuation of application Ser. No. 07/025,896 filed Mar. 13, 1987, now U.S. Pat. No. 4,974,162.

BACKGROUND OF THE INVENTION

The present invention is directed to a technique for processing electrocardiagram signals, and more particularly to a technique for diagnosing myocardial ischemia.

The detection and localization of reversible myocardial ischemia (low heart blood flow which causes reduced oxygen delivery to the heart) of minimal to moderate degree is a major goal in the identification of potential candidates for coronary artery revascularization before ischemic infarction (death of heart muscle) or arrhythmias develop. Although local cardiac effects of various kinds can be captured from epicardial array ECG records, from a clinical and experimental point of view it is highly desirable to have an ECG signal processing methodology that will generate a set of quantifiable ECG variables which can be used for the delineation of ischemic myocardium and the evaluation of its severity.

Unfortunately, present ECG signal analysis for ischemia detection is largely heuristic, too ambiguous to permit a reasonably uniform implementation in computer programs and often not diagnostic prior to myocardial damage. Most ECG processing schemes have adopted a simplified approach for representing ECG waveforms using decision variables based on measurements of the time of ECG wave duration, and the amplitude and slope characteristics. See, for example, J. M. Jenkins, Automated Electrocardiography and Arrhythmia Monitoring, Prog. Cardiovas. Dis., vol. 5, p.367, 1983 (hereinafter reference 1); J. Euderle, M. Telerman, K. Chesky and H. Jaffe, Computer Interpretation of Electrocardiograms and Vectocardiograms, Advances in Cardiology, vol. 16, p.194, 1976 (reference 2); U. Jain, P. M. Rautaharju and B. M. Horacek, The Stability of Decision Theoretic Electrocardiographic Classifiers Based On the Use of Discretized Features, Comp. Biomed. Res., vol. 13, p.695, 1980 (reference 3); C. Laxer, R. E. Ideker and T. C. Pilkington, The Use of Unipolar QRS Potentials To Estimate Myocardial Infarction, IEEE Trans. Biomed. Engin., vol. BME-32(1), January 1985 (reference 4); and F. J. Claydon, III, T. C. Pilkington and R. E. Ideker, Classification of Heart Tissue From Bipolar and Unipolar Intramural Potentials, IEEE Trans. Biomed. Engin., vol. BME-32(7), July 1985 (Reference 5). To this end also, many investigators have used various ECG signal mapping procedures for the detection of myocardial ischemia from array ECG signals, either epicardial or torso. The most widely used procedures are isopotential mapping as described by S. Rush and others in papers appearing in Body Surface Mapping of Cardiac Field, Advances in Cardiology, vol. 10, 1974, (Reference 6) isochronic mapping as described by D. Durrer, R. T. Van Dam, G. E. Freud, M. J. Janse, F. L. Meijler, and R. C. Arzbaecher, Total Excitation of the Isolated Human Heart, Circulation, vol. 41, pp.899–912, June 1970 (Reference 7), TQ-ST segment mapping and regional monophasic action potentials and their first derivatives, as described by M. R. Franz, J. T. Flaherty, E. V. Platia, B. H. Bulkley, and M. L. Weisfeldt, Localization of Regional Myocardial Ischemia By Recording of Monophasic Action Potentials, Circulation, vol 69, pp.593–604, March 1984 (Reference 8). However, these approaches are fundamentally simple and to some respect primitive methods that do not take into account the probabilistic nature associated with decision making procedures. At best, mapping procedures are characterized by a small number of salient features such as the number and location of potential extrema, as described by F. A. Roberge, Some Emerging Issues In Electrocardiology, Proc. Special Symp. on Critic Emerg. Issues in Biom. Engin., C. J. Robinson and G. V. Kondraske (editors), pp. 59–61, IEEE Press No. 86CH2369-7, November 1986 (Reference 9). They are not easily interpreted as a whole and do not effectively use all of the experimentally measured information. Finally, since all the aforementioned schemes operate in the time-domain of the data, they are vulnerable to measurement errors in baseline detection, and locating onsets and offsets of ECG waves in the presence of noise. This is described by F. Kornreich, P. M. Rautaharju, J. W. Warren, B. M. Horacek, and M. Dramaix, Effective Extraction of Diagnostic ECG Waveform Information Using Orthonormal Basis Functions Derived From Body Surface Potential Maps, Journ. Electrocardiol., vol. 18(4), pp.341–350, 1985 (Reference 10). There has also been ample evidence concerning the weak robustness of these approaches, as described, for example, by R. R. Helppi, V. Unite, and H. K. Wolf, Suggested Minimal Performance Requirements and Methods of Performance Evaluations For Computer ECG Analysis programs, CMA Journ., vol. 108, p.1251, 1973 (Reference 11).

The frequency content of ECG signals has been used to detect myocardial pathology as an alternative approach to time domain techniques. This has been described by T. L. Nichols, and D. M. Mirvis, Frequency Content of the Electrocardiogram. Spatial Features And Effects of Myocardial Infarctions. Journ. Electrocardiology, vol. 18(2), pp.185–194, 1985 (Reference 12). In this study of array ECG signals, the spatial variation in the frequency content of the electrocardiogram was mapped and found to be affected by myocardial infarction. However, no decision variables were identified which permit quantitative localization or probabilistic decision-making.

The detection of non-infarcting reversible ventricular ischemia, but not its localization, has been done by application of an advanced signal processing methodology which deals with an ECG array as a multidimensional power frequency spectrum. See, for example, C. L. Nikias, M. R. Raghuveer, J. H. Siegel, and M. Fabian, The Zero-delay Wavenumber Spectrum Estimation For the Analysis of Array ECG Signals - An Alternative to Isopotential Mapping, IEEE Trans. Biomed. Engin., vol. BME-33(4), pp.435–452, April 1986 (Reference 13); J. H. Siegel, C. L. Nikias, M. R. Raghuveer, M. Fabian, K. C. Goh, and D. Sanford, Epicardial Electrical Activation Analyzed Via Frequency-Wavenumber Spectrum Estimation For the Characterization of Arrhythmiagenic States, Journ. Electrocardiology (to be published 1987) (Reference 14); C. L. Nikias, and J. H. Siegel, Knowledge Based Classification of Epicardial Electric Activation From Array ECG Signals, Proc. 12th Northeast Bioeng. Conf., pp.198–200, Yale University, March 1986 (Reference 15); and C. L.

Nikias, J. H. Siegel, M. R. Raghuveer, and M. Fabian, Spectrum Estimation For the Analysis of Array ECG. Proc. 7th Annual Int. Conf. IEEE Engin. in Medicine and Biology, pp.824–829, Chicago, Ill., September 1985 (Reference 16). This method allows for the computation and compact graphic display of frequency-wavenumber spectrum estimates (FWSE) of array ECG signals by the use of a Zero-Delay Wavenumber Spectrum Estimation (ZDWS) technique (e.g., see References 13 and 14). It has been demonstrated that the ZDWS method provides a means for objective quantification of the alterations in cardiac activation produced by areas of myocardial ischemia because key parameters associated with abnormalities in electrical wavefront propagation are easily revealed in the spectrum domain by analysis using the form of a hierarchical tree structure (e.g., see Reference 15). The ZDWS method does not require uniformly spaced sensors and can accommodate any shape of ECG array. Successful experimental and clinical use of the FWSE method to the analysis of epicardial as well as human body surface array ECG signals has been presented (e.g., see References 13, 14, & 16). Its application to the inverse problem of electrocardiography also has been shown, e.g., as described by C. L. Nikias, T. Y. Shen and J. H. Siegel, Frequency-Wavenumber Invers Model For Electrocardiography, Proc. 8th Annual Int. Conf. IEEE Engin. in Medicine and Biology, pp.307–310, Dallas-Fort Worth, Tex., November 1986 (Reference 17).

However, while specific for detection of ischemic modulation of ventricular activation characteristics, the multidimensional nature of the ZDWS technique does not permit localization of ischemic areas, nor does it allow for a direct comparison of ischemia quantification with biochemical parameters of the ischemic myocardium as related to specific sensor locations. Moreover, none of the previously mentioned methods permit the use of probability analysis statistics of the Bayesian type to quantify the likelihood of correct detection of a given area as ischemic, compared to its probability of being normal.

Accordingly, it is an object of the present invention to develop an advanced ECG signal processing methodology which could be directly used to detect, localize and quantify the level of biochemical severity of areas of ischemic myocardium.

SUMMARY OF THE INVENTION

The present invention comprises a new method of analysis which transforms the epicardial array monopolar ECG signals into the multichannel spectrum domain and identifies decision variables from the autospectra. The present invention further comprises a computer-based methodology to detect and localize the epicardial projections of ischemic myocardial ECGs during the cardiac activation rather than repolarization, phase which is suitable for use in experimental research and in surgical, or non invasive, studies in humans. This is done by transforming ECG signals from an epicardial or torso sensor array into the multichannel spectral domain and identifying any one or more of a plurality of decision variables. The preferred variables discussed herein include: (1) the frequency in Herz of the spectral peak ($f_0$), (2) its frequency bandwidth 50% below the peak value ($w_0$), and (3) the maximum eigenvalue difference of the signal's autocorrelation matrix ($e_0$). (4) the maximum difference in consecutive lags of the signal's AC sequence ($r_0$). (5) the sum of the squares ($C_J$) of the first J reflection coefficients (for any J=1,2 . . . ,M) which are computed by the Levinson-Durbin algorithm assuming an Mth-order autoregressive (AR) model and using as input data the first (M+1) autocorrelation lags of the ECG signal. The value of M can be selected anywhere between 6–10. (6) The variance of the linear prediction errors $V_J = P_J$ for any J=1,2 . . . ,M which is computed by the Levinson-Durbin algorithm assuming an Mth-order AR model and using as input data the first (M+1) autocorrelation lags of the ECG signal. (7) The entropy of the ECG signal $E_J$ for any J=1,2 . . . ,M which is by definition the product of the first J variances of the linear prediction errors, i.e., $E_J = V_1 \cdot V_2 \ldots V_J$ where $v_i = P_i$. Using the histograms of each of the decision variables (e.g., $f_0$, $w_0$ and $e_0$, etc.) of ECGs from normal and from ischemic areas of myocardium it is possible to predict ischemia in a new Test group of subjects from any Bayesian test (or any of its special cases) where the threshold probabilities for each variable of detecting ischemia are compared to that of detecting normal. This method has been experimentally verified by quantification of heart sensor areas by a Bayesian test which revealed that, compared to normal control, ECG spectra with decreased $f_0$ and $w_0$ and increased $e_0$ relative to their respective thresholds had increased myocardial lactate ($p<0.005$), decreased ATP ($p<0.05$) and reduced creatine phosphate ($p<0.005$). Prediction of the decision variable ($p<0.0001$) as a continuous variable could be obtained from regression of the myocardial levels of ATP plus creatine phosphate demonstrating that these decision variables appear to directly reflect myocardial energetics. This advanced signal processing method for ECG array data can be used to detect, localize and quantify reversible myocardial ischemia.

In the one embodiment, two decision variables are used, i.e., the location of the spectral peak ($f_0$) and its width 50% below the peak value ($w_0$). The present inventors have discovered that during normal epicardial activation the frequency peak in Herz (Hz) lies at higher Hz [20 Hz $< f_0 <$ 50 Hz] and the frequency spectral range is wide [20 Hz $< w_0 <$ 45 Hz] whereas during myocardial ischemia the spectrum of frequencies shifts to a lower peak [0 $< f_0 <$ 15 Hz] and the frequency spectral range narrows [0 $< w_0 <$ 20 Hz]. Using the histogram of the $f_0$ and $w_0$ parameters of 1260 ECGs from normal and 850 from ischemic areas of myocardium obtained from a group of ischemia study animals, it was possible to predict ischemia in a new test group of animals from a Neyman-Pearson test where the threshold probability of missing ischemia is 0.002 and the probability of detecting a normal condition is greater than 0.94.

BRIEF DESCRIPTION OF THE DRAWINGS

The invention will be more clearly understood from the following description in conjunction with the accompanying drawings, wherein:

FIG. 1(a) is an illustration of a monopolar ECG signal in the time domain, for normal (control) conditions, with FIG. 1(b) illustrating the same signal for ischemic conditions;

FIGS. 2(a) and (b) are representations of the signals in FIGS. 1(a) and 1(b), respectively, in the frequency domain, showing the estimation of peak frequency $f_0$ and frequency spectrum width $w_0$;

FIGS. 3(a) and (b) are representations of the signals of FIGS. 1(a) and (b), respectively, in the autocorrelation domain;

FIGS. 4(a)–4(c) illustrate the derivation of autocorrelation eigenvalues and eigenvalue differences of the autocorrelation matrix for computation of maximum eigenvalue difference ($e_0$);

FIGS. 7–13 are flow charts illustrating in more detail the various steps in FIG. 6, with FIG. 12(a) illustrating the Levinson-Durbin algorithm employed in Step 18 in FIG. 13;

FIGS. 23(a)–23(c) illustrate experimental conditions and test evaluation results for normal (control) conditions based on a decision variable $f_0$;

FIGS. 24(a)–24(c) illustrate the same experimental test evaluation results as in FIGS. 23(a)–23(c), respectively, for localized ischemia;

DETAILED DESCRIPTION OF THE PREFERRED EMBODIMENT

Figure 5:
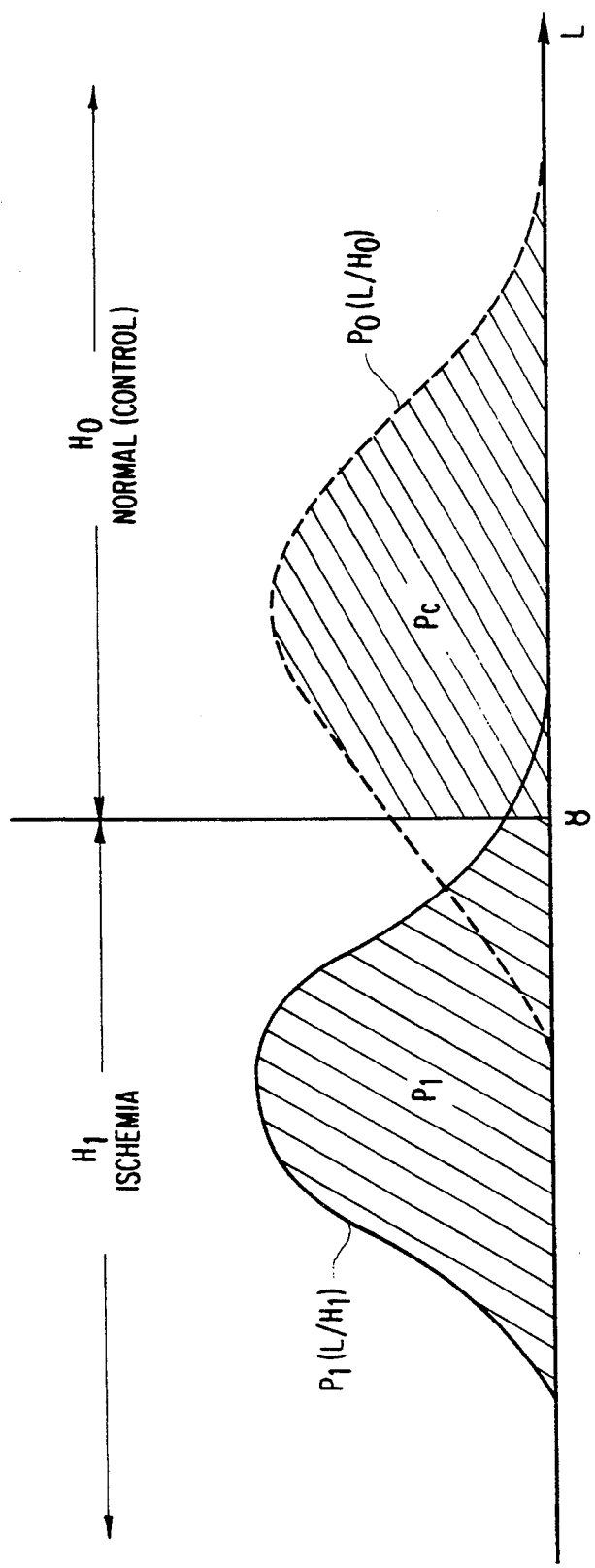
FIG. 5 illustrates the probability density function of a decision variable during ischemia ($P_1$) and during control ($P_0$), with a threshold value ($\gamma$) for decision statistic L, wherein $P_I$ and $P_C$ are probabilities for a prechosen threshold value in a Neyman-Pearson test, L is the decision statistic and $P_1$ (L/$H_1$), and $P_0$(L/$H_0$) are the assumed probability density function of L under $H_1$, $H_0$, respectively.

The ECG signal processing technique according to the present invention employs a new application of Frequency Wavenumber Spectral Estimation (FWSE) techniques previously applied by the present inventors to the multidimensional analysis of the number, direction, velocity and frequency characteristics of depolarizing cardiac activation currents as projected on the epicardial surface of the heart, the previous techniques having been described in References 13–16. However, in the method of the present invention the individual epicardial array sensor ECG signals are considered as a multichannel time series rather than a multidimensional signal. The difference, critical for ischemia localization, is that while both multichannel and multidimensional spectral estimation techniques transform the time based ECG activation signal into the frequency spectrum domain, the multichannel spectral analysis (MCSA) is a vector valued function of a scalar variable (time) which transforms the time axis of a multisensor array into the frequency domain while retaining the spatial localization of the original sensor array. In contrast, the multidimensional signal analysis previously reported in References 13 and 14 is a scalar function of two or more variables (usually one is time and the others are space variables). Using a multichannel approach treats the entire array globally to establish the characteristics of the depolarization without regard to individual sensor locations.

In the preferred embodiment of the present invention, the Multichannel Spectral Analysis (MCSA) technique derives a set of quantitative parameters from FWSE transformation of the time-domain ECG signal of each array sensor into the spectrum domain and into the autocorrelation domain of the data. In the example given, three new decision variables are created, two from the spectrum domain (the peak frequency $f_0$ and spread of frequencies $w_0$) and one from the autocorrelation (AC) domain the maximum eigenvalue difference $e_0$ of the AC matrix ECG signal decay. These decision variables are quantitative descriptors of the information content of the original time based ECG activation signal.

FIGS. 1–3 illustrate these three domains from epicardial monopolar ECG recordings using two typical records of data, Normal, i.e., control (FIGS. 1(a), 2(a) and 3(a)) and reversible ischemia (FIGS. 1(b), 2(b) and 3(b)). From these Figures, it is apparent how changes due to ischemia in the time-domain are mapped into the spectrum or autocorrelation (AC) domains. FIGS. 4(a)–4(c) illustrate the eigenvalues and eigenvalue differences of the AC matrix of the ECG recordings shown in FIGS. 1(a) (control) and 1(b) (ischemia). From FIGS. 1–4 we have the following important observations:

1) During normal (control) activation the power spectrum, or frequency content, (FIG. 2(a)) of the epicardial monopolar ECG signal exhibits a bell-shaped power distribution, in this particular example with a peak at $f_0$=31.84 Hz (about 32 msec wave duration in the time-domain) and frequency spectrum width $w_0$ 50% below peak value at $w_0$=24 Hz. On the other hand, during ischemia there is a reduction in total high frequency power distribution. As a result, there is a shift in location of the peak towards low frequencies as well as a sharpening of the peak without a significant change in the magnitude of the peak. In other words, myocardial ischemia results in decreased values for both $f_0$ and $w_0$, e.g., $f_0$=10.20 Hz (about 100 msec wave duration) and $w_0$=11.00 Hz for the illustrated example. In the case of light ischemia, it is possible to observe a reduction in the value of $f_0$ without any change in $w_0$.

2) The autocorrelation (AC) sequence of the ECG signal decreases slowly during ischemia (FIG. 3(b)) and much faster during control (FIG. 3(a)).

3) The normalized eigenvalues of the AC matrix of the ECG signal decay much faster during ischemia (FIG. 4(b)) than during control (FIG. 4(c)). Normalizing the initial eigenvalue to one, the maximum eigenvalue difference $e_0$ during ischemia is $e_1$=0.8456195, whereas during control, the maximum $e_0$ is $e_2$=0.5467806, where $e_0$=maximum [$e_1,e_2,e_3,e_4\ldots e_N$].

The important observations stated above clearly suggest that the location of the spectral peak $f_0$ and its frequency width 50% below peak value $w_0$ are two important spectrum domain decision variables which can be used for detection and quantification of reversible myocardial ischemia. Furthermore, the maximum slope of the normalized eigenvalues $e_0$ of the AC matrix (defined in FIGS. 3(a) and 3(b)) is yet another decision variable which incorporates some hypothesis-discriminating power in the AC domain.

One of the advantages of using quantitative variables for decision making is that their subsequent statistical analysis can establish the probability that a detected event has occurred as a binary chance. This binary hypothesis problem can be presented as the null hypothesis ($H_0$) being control (or normal activity) and the positive hypothesis ($H_1$) being the chance of ischemia. Let us also assume that a recorded epicardial monopolar ECG signal is $\{X(n)\}$, $n=1,2,\ldots,N$. The challenging question is how to generate a decision variable (L) from the recorded ECG signal such that reliable detection of probability can be facilitated. Let us assume that L is generated following a judicious mechanism $F(.)$, i.e., $L=F(x(1),\ldots,x(n))$. In order to make a decision, the decision variable is compared to the threshold value ($\gamma$) as follows:

$$\begin{array}{c} H_0 \\ L \gtrless \gamma \\ H_1 \end{array} \quad (2)$$

indicating that if L is greater than $\gamma$ then the ECG signal is normal, and if L is less than $\gamma$ the signal is ischemic. The test can be repeated for all ECG signals in an array of electrodes. It should be noted that the value of $\gamma$ is of primary importance in reliably detecting the true event. It can be chosen using the general Bayes criterion or its special cases, i.e., minimum error probability, mini-max or Neyman-Pearson. In the example here, we chose to assume a Neyman-Pearson test as it does not require any a priori probabilities, or costs, about the two possible outcomes.

If we denote as $P_1(L/H_1)$ the probability density function (PDF) of the decision variable L during ischemia and $P_0(L/H_0)$ the PDF of L during control, the following probabilities may be defined for a prechosen value of $\gamma$:

$$P_c \equiv Pr(H_0 \text{ occurs and } H_0 \text{ is detected}) = \int_\gamma^\infty P_0(x/H_0)dx$$

$$P_I \equiv Pr(H_1 \text{ occurs and } H_1 \text{ is detected}) = \int_{-\infty}^\gamma P_1(x/H_1)dx$$

In other words, $P_C$ is the probability of detecting normal activation during control and $P_I$ is the probability of detecting ischemia when the signal is ischemic. FIG. 5 illustrates a sketch of the two PDFs and the definition of $P_I, P_C$. The general objective is to maximize $P_I$ for a constant $P_C$. The goal of the present invention is to identify judicious mechanisms $F(.)$, i.e., detection schemes, such that $P_I$ and $P_C$ of decision variable L are as close to 1.0 as possible. The Neyman-Pearson test will allow us to see how the two probabilities ($P_I, P_C$) change with threshold and thus compare the performance of the various detection schemes.

A detailed methodology for the present invention will now be described. While the description will deal with the derivation and use of certain preferred decision variables, it should be appreciated that other variables may be useful as well and that the invention is not to be limited only to the specific variables discussed herein.

Figure 6:
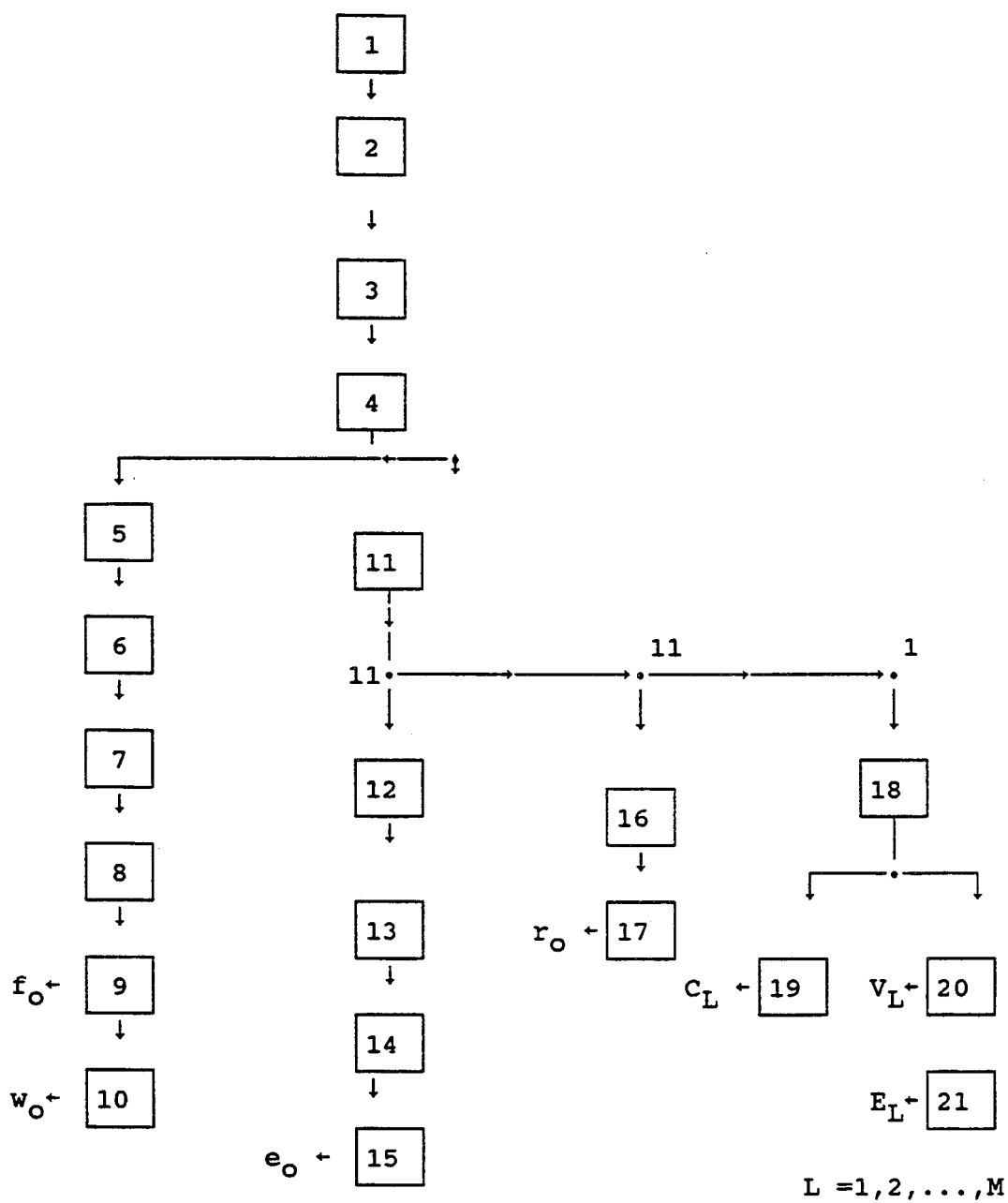
FIG. 6 is an overview flow chart for the derivation of various decision variables.

FIG. 6 is a flow chart providing an overview of a sequence of steps which may be used to implement various examples of the present invention. The flow chart illustrates the processing of the signal from a single ECG signal, although it will be remembered that for proper localization the present invention will preferably process signals from an array of sensors. Our description will first concern the flow path made up of steps 1-10 whereby an ECG signal is evaluated using decision variables $f_0$ and/or $w_0$.

Figure 7:
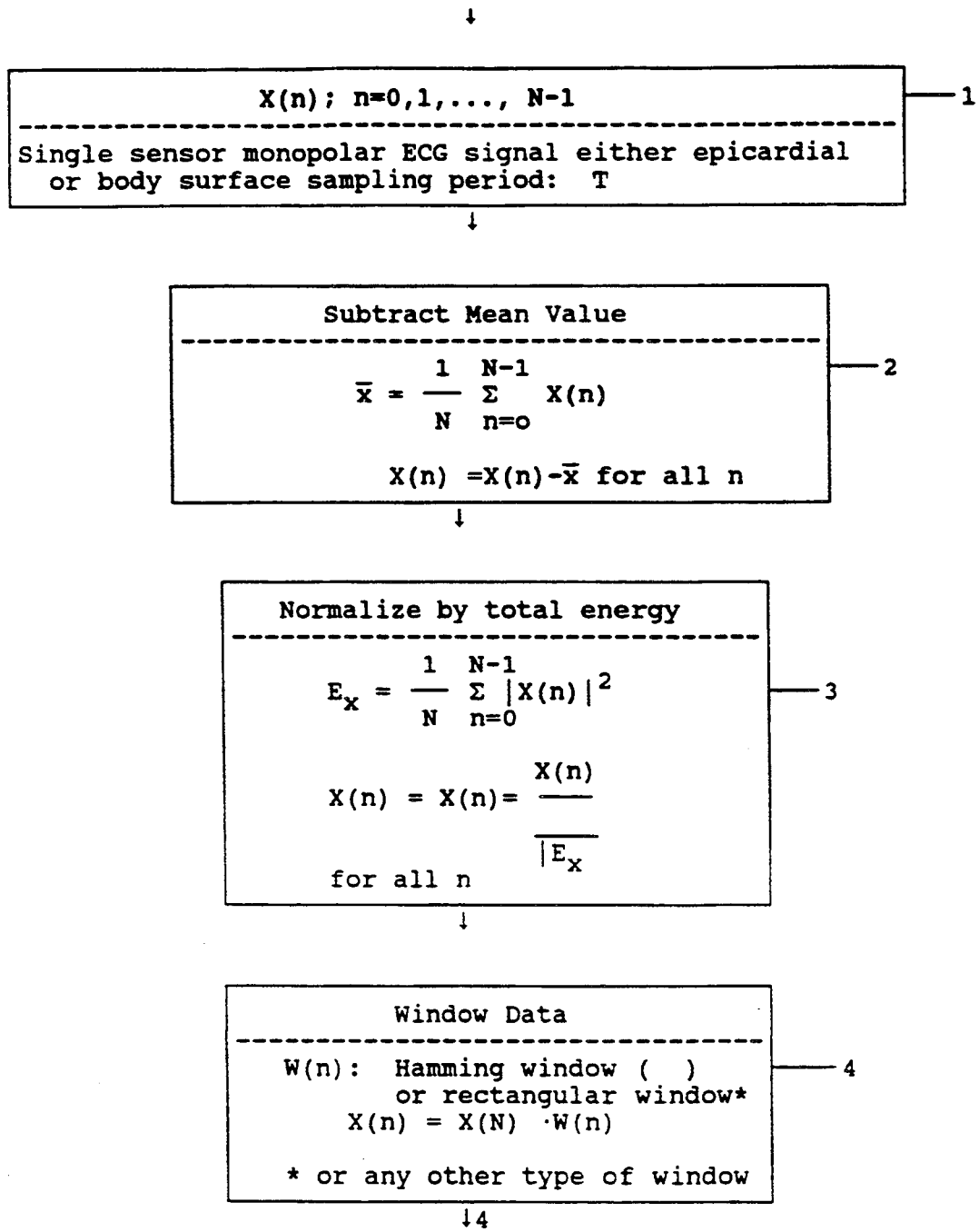

Steps 1-4 are illustrated in greater detail in FIG. 7. As shown therein, Step 1 comprises the obtaining of a single sensor monopolar ECG signal, either epicardial or body surface. The signal comprises a series of samples $X(n)$; $n=0,1,\ldots,N-1$, with sampling period T.

In Step 2, the mean value of the samples is calculated and is then subtracted from each sample, and in Step 3 the total energy of the samples is calculated and this calculated total energy is then used to normalize all samples. In Step 4, the data are window processed using a Hamming window, or some other suitable window.

Figure 8:
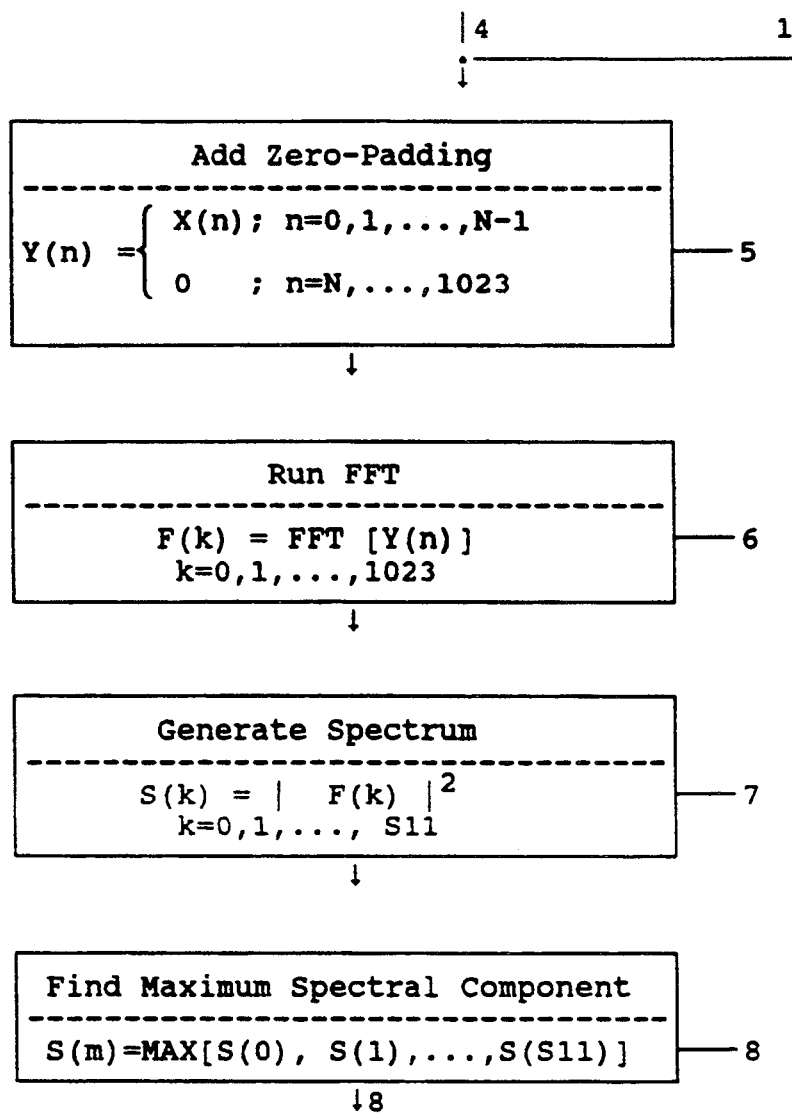

Referring now to FIG. 8 which illustrates Steps 5-8 of FIG. 6, in Step 5 zero-padding is performed to prepare the data for a Fast Fourier Transform (FFT) which is then performed in Step 6 to convert the time domain signals to the frequency domain. In Step 7, the power spectrum is generated, and in Step 8 the maximum spectral component is determined.

The specific implementation of each of Steps 1-8 will be known to those of skill in the art and need not be described in further detail herein. The end result of these steps 1-8 is to convert time-domain signals such as in FIGS. 1(a) and 1(b) into the spectrum domain as shown in FIGS. 2(a) and 2(b), respectively.

Figure 9:
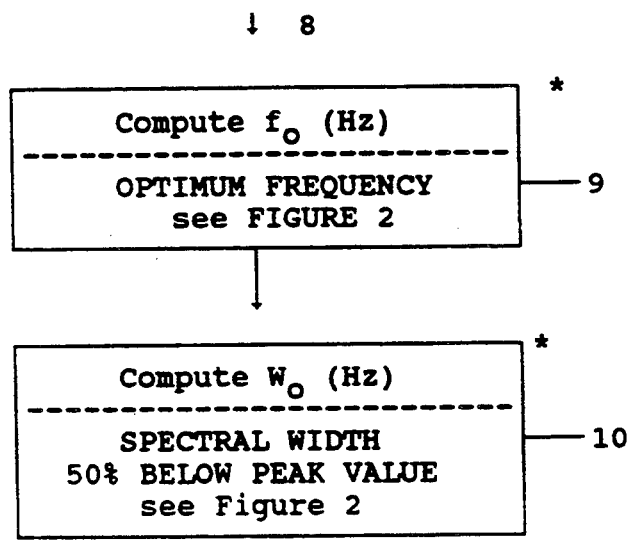

Turning now to FIG. 9, in Step 9 the peak frequency $f_0$ in FIGS. 2(a) and 2(b) is computed. If desired, in Step 10 the width $w_0$ at 50% below peak value is computed. The calculations of $f_0$ and $w_0$ will be straightforward to one of skill in the art and need not be described in detail herein. The decision variable $f_0$ or $w_0$ from each sensor is then compared to a threshold level which, as described earlier, has been optimally selected from statistical studies, i.e., empirically, to yield the most accurate decision results.

If the maximum eigenvalue difference $e_0$ is to be used as the decision variable, the path comprising steps 1-4 and 11-15 in FIG. 6 is followed. Steps 1-4 have been described above and are illustrated in FIG. 7. As shown in FIG. 10, Step 11 involves the estimation of the autocorrelation (AC) sequence, $\{R(m)\}$, of the ECG data $\{X(n)\}$, $n=1,2\ldots,N$, which could be estimated by $$R(m) = \frac{1}{N} \sum_{n=1}^{N-1-m} X(n) X(n+m); m = 1, 1, \ldots, M \quad (1)$$

In Step 12, the AC matrix is formed. The matrix of the ECG signal is Toeplitz and symmetric and can be easily formed from equation (1) above using $\{R(0), R(1) \ldots, R(M)\}$. In Step 13, the eigenvalues of the AC matrix R are calculated. As shown in FIG. 11, Step 14 involves the computation of eigenvalue differences, with Step 15 comprising the determination of the decision variable $e_O$, the maximum eigenvalue difference. An example of the eigenvalues calculated in Step 13 is shown in FIG.

4a, with the eigenvalue differences for ischemia and control being shown in FIGS. 4b and 4c.

Figure 12:
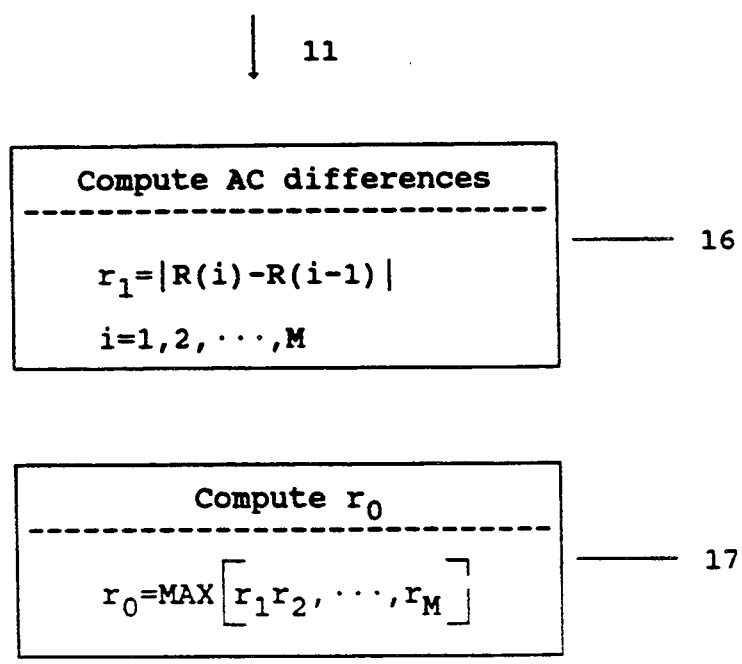

Referring now to FIG. 12, a further potential decision variable is the maximum difference $r_0$ between consecutive lags of the signal's AC sequence. To utilize this decision variable, the flow path through the overview chart of FIG. 6 is followed through Steps 1–4 and 11 to obtain the estimated AC sequence. The differences $r_i$ are calculated in Step 16, and the maximum difference is then calculated in Step 17.

Figure 12A:
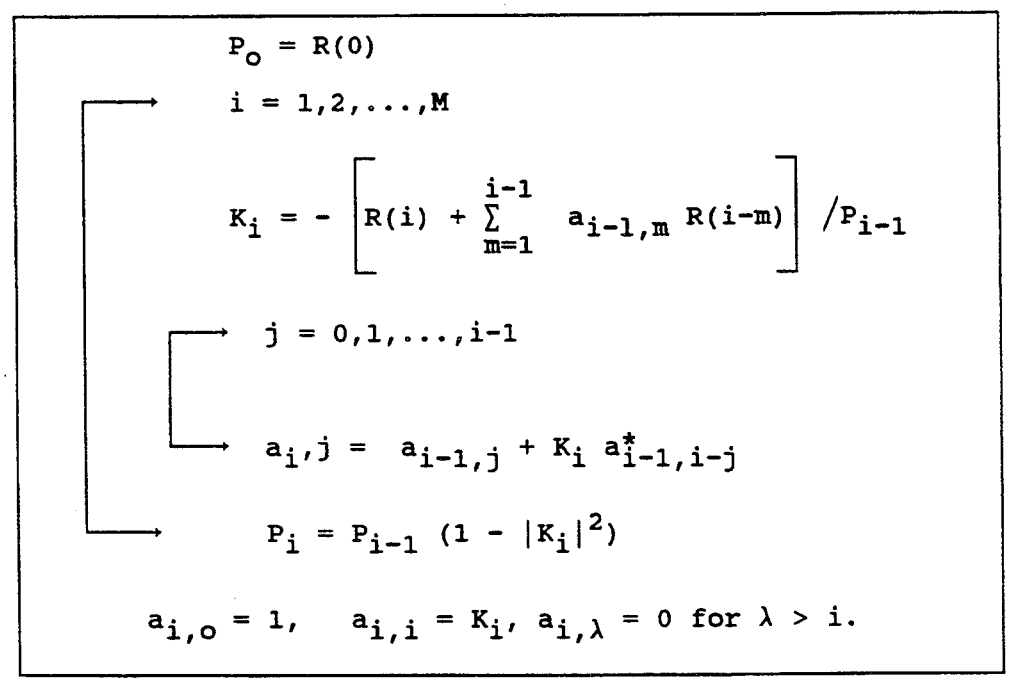

A further decision variable is the sum ($C_j$) of the squares of the first J reflection coefficients (for any J = 1,2, ... ,M) which are computed by the Levinson-Durbin algorithm assuming Mth-order autoregressive (AR) model and using as input data the first (M+1) autocorrelation lags of the ECG signal. For convenience, this algorithm is set forth in FIG. 12(a). The value of M can be selected anywhere between 6 and 10. To utilize this decision variable, the flow path through the overview chart of FIG. 6 is followed through Steps 1–4 and 11, and then proceeds through steps 18 and 19 which are illustrated in greater detail in FIG. 13. In Step 18, the Levinson-Durbin algorithm is run to obtain the reflection coefficients, and in Step 19 the sum of the squares is calculated.

Figure 13:
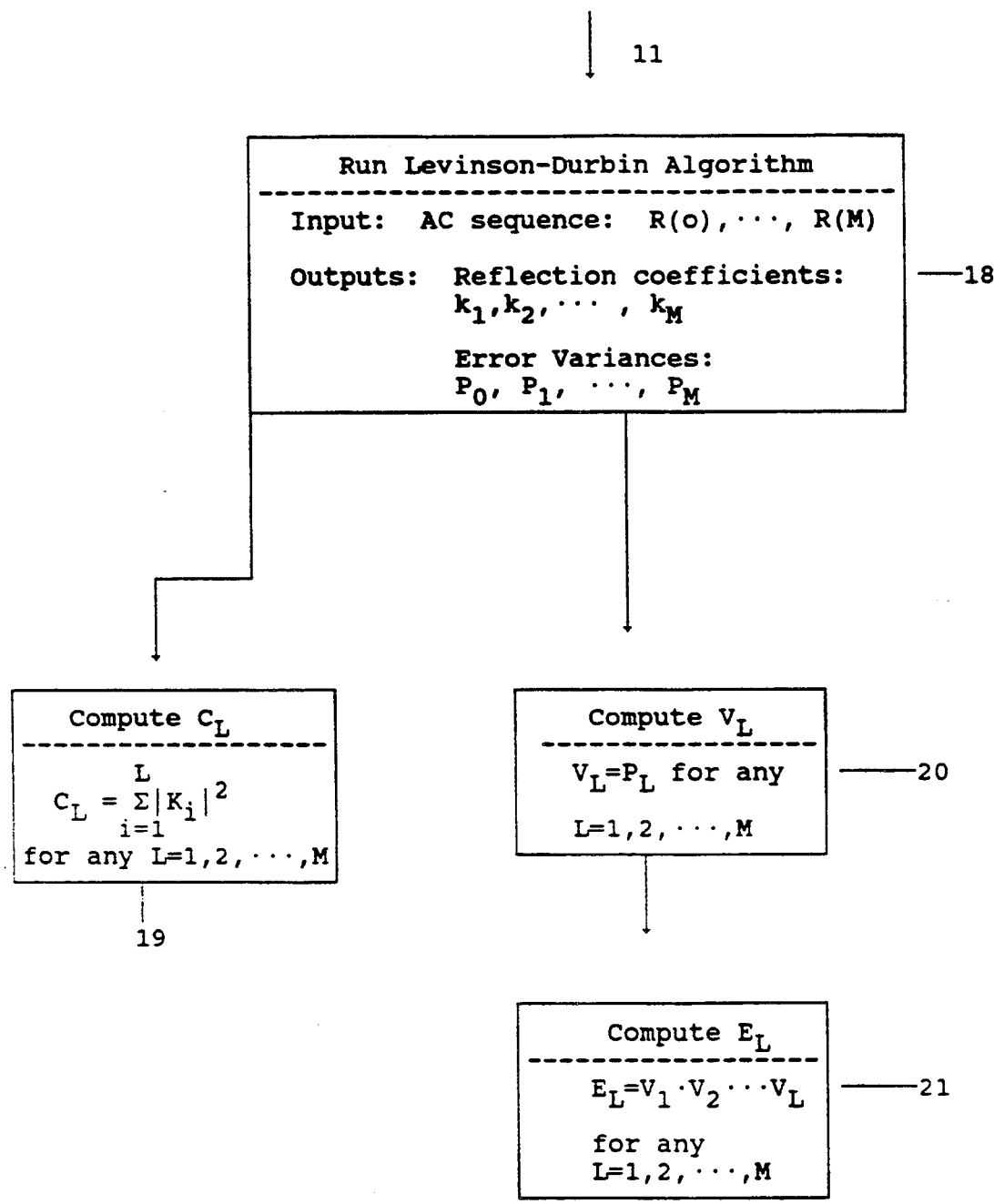

In Step 18, the error variances $P_0, P_1, \ldots, P_M$ are also obtained, and these can be used directly as a further decision variable, as shown at Step 20 in FIG. 13.

Finally, a further potential decision variable would be the entropy of the ECG signal $E_J$ for any J = 1,2, ... ,M which is by definition the product of the first J variances of the linear prediction errors. This is shown at Step 21 in FIG. 13.

After deriving the desired decision variables, their histograms must be generated. When analyzing decision variables, the usual assumption made in the literature is that their probability density functions (PDF's) during control and ischemia are Gaussian. However, this assumption is for convenience and is not necessarily correct. Given a population of normal ECG signals and a population of ischemic signals, it is preferable to compute the actual histograms of the PDF's for each one of the decision variables and, based on these histograms, perform detection and quantification of ischemia.

Figure 14:
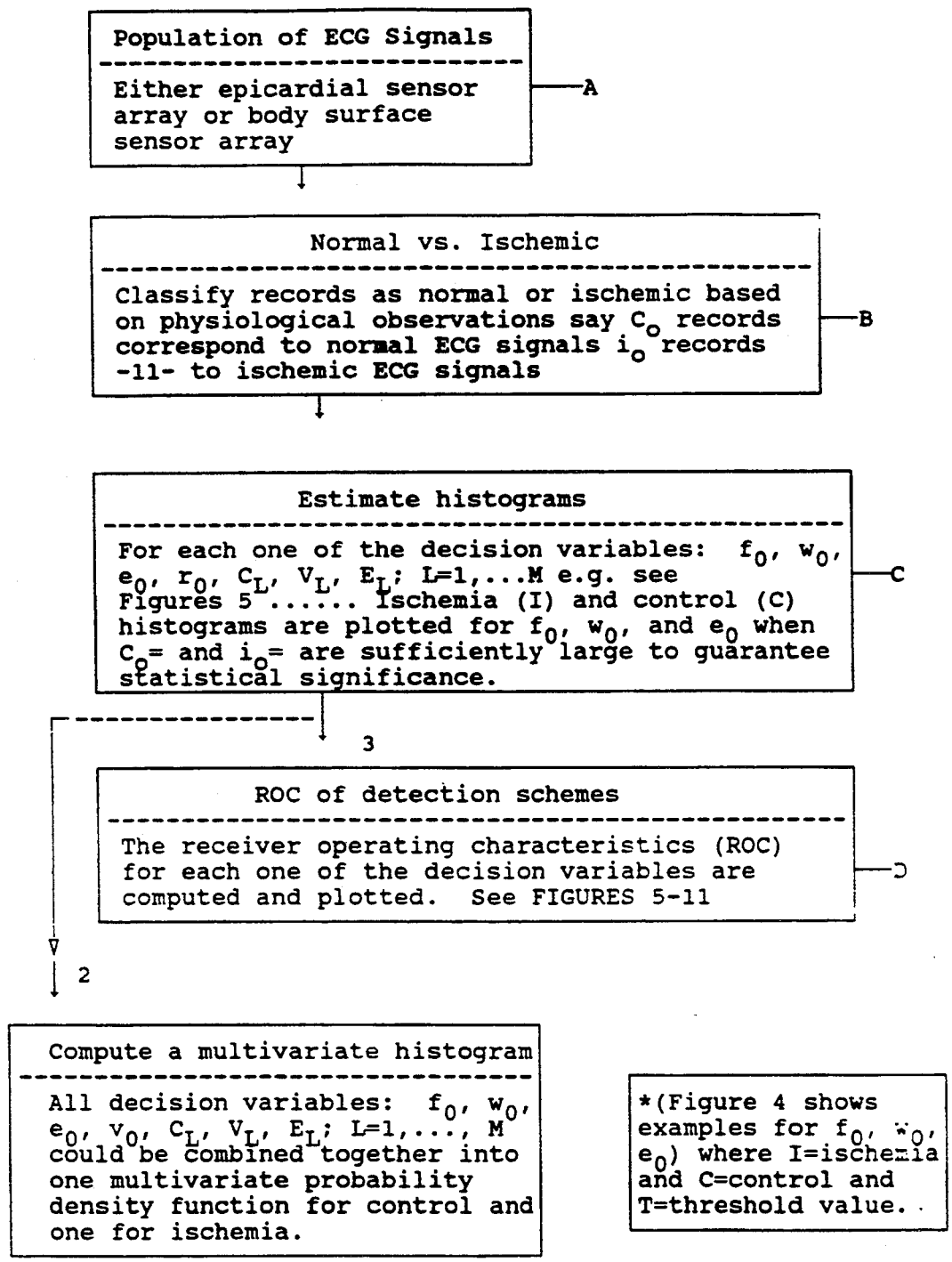
FIG. 14 is a flow chart illustrating the generation of histograms of the decision variables.
Figure 15A:
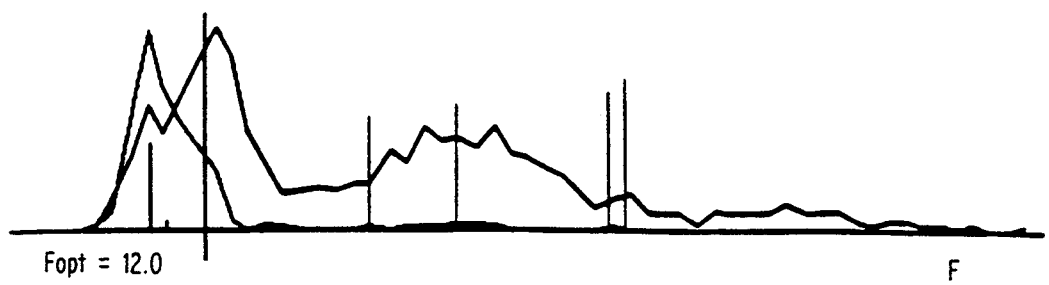
FIGS. 15(a)–15(c) illustrate histograms of experimentally obtained probability density functions under control (C) and ischemic (I) conditions for peak frequency optimimum ($f_0$), frequency width optimum ($w_0$) and autocorrelation eigenvalue difference optimum ($e_0$). Note threshold (T) value of $\gamma$ and location of individual sensors (shorter lines) with regard to T in the probability density functions. Note also that none of the histograms has a Gaussian distribution.
Figure 15B:
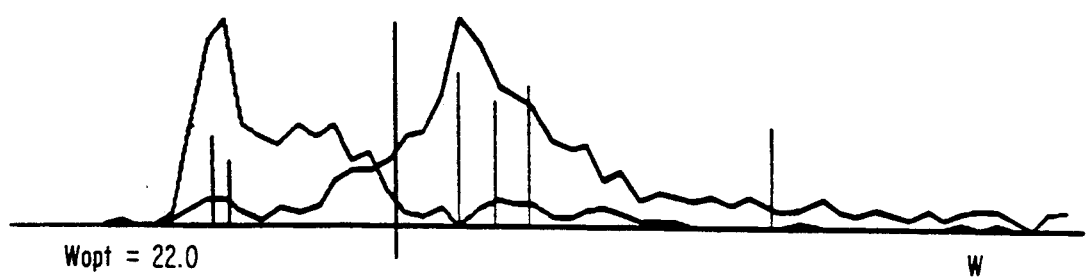
Figure 15C:
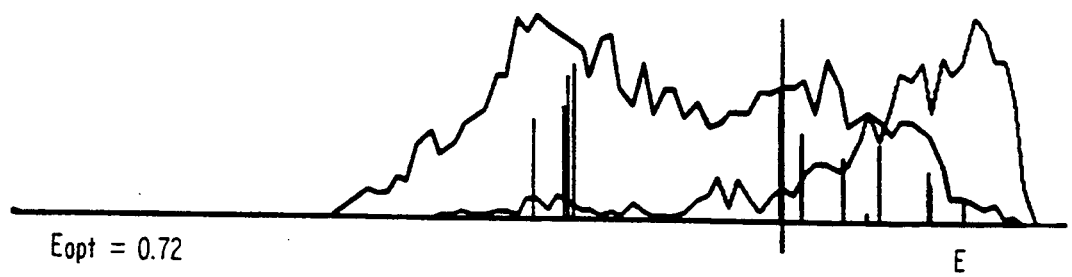
Figure 16:
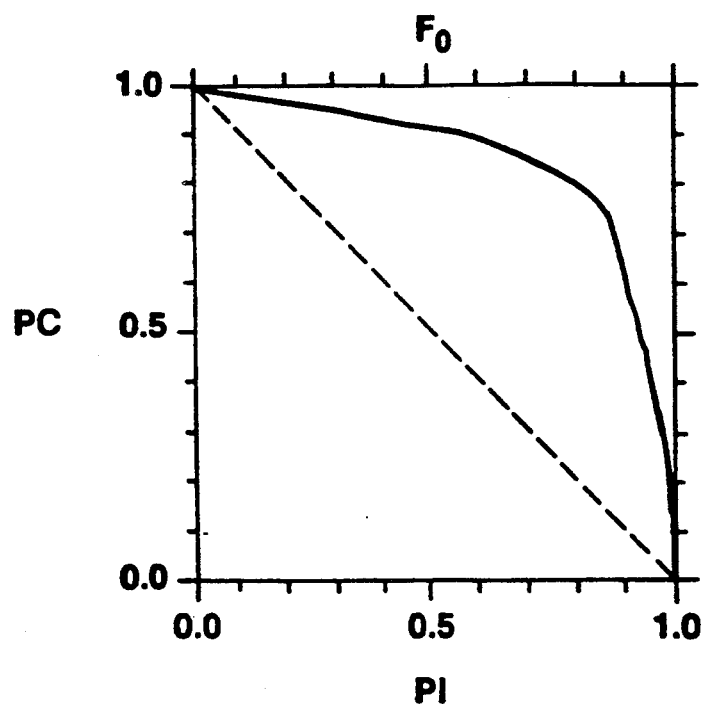
FIGS. 16–22 are examples of plots of the receiver operating characteristics for each of the decision variables.
Figure 17:
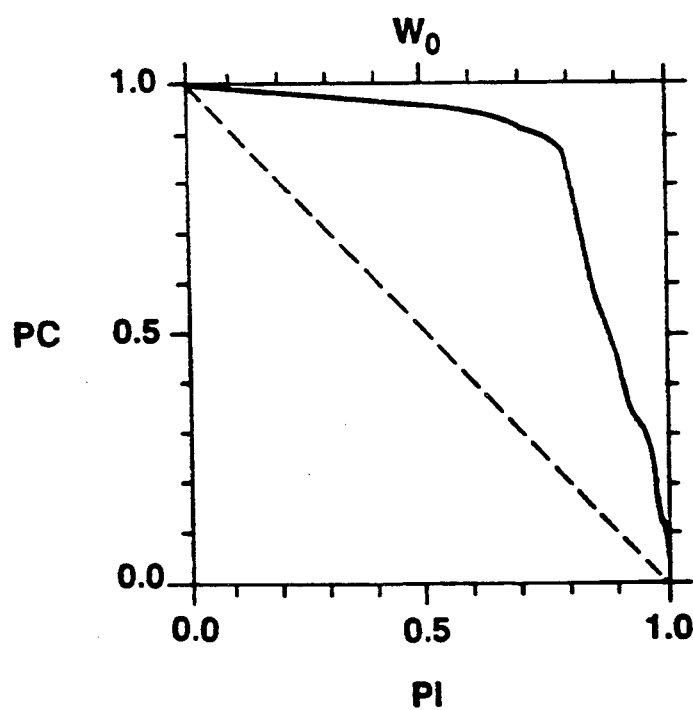
Figure 18:
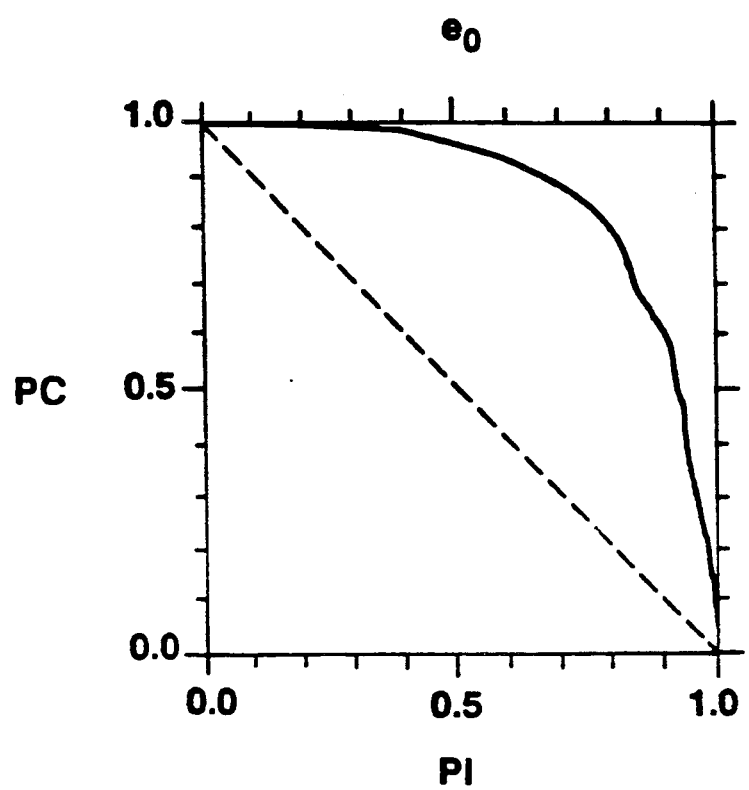
Figure 19:
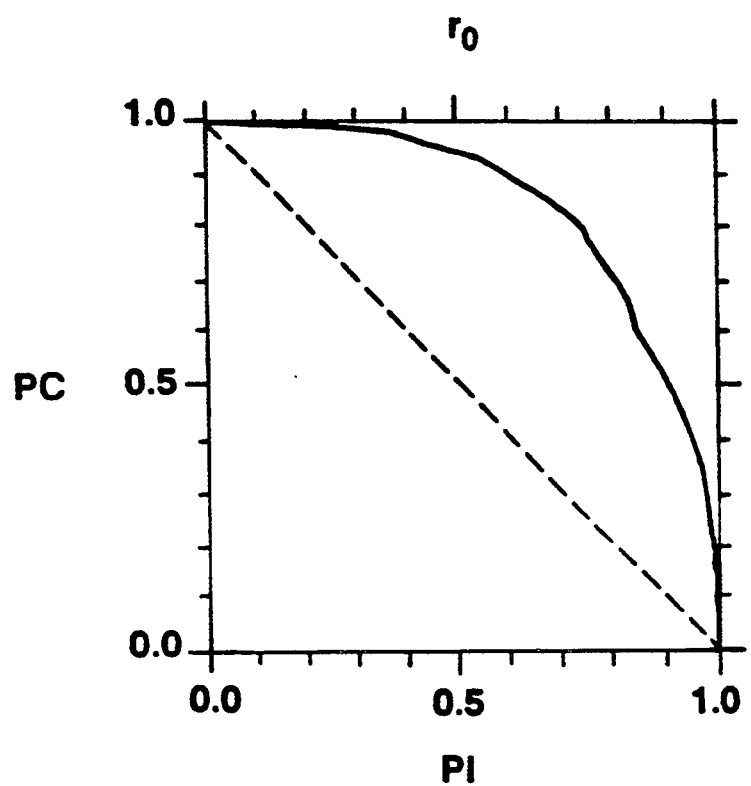
Figure 20:
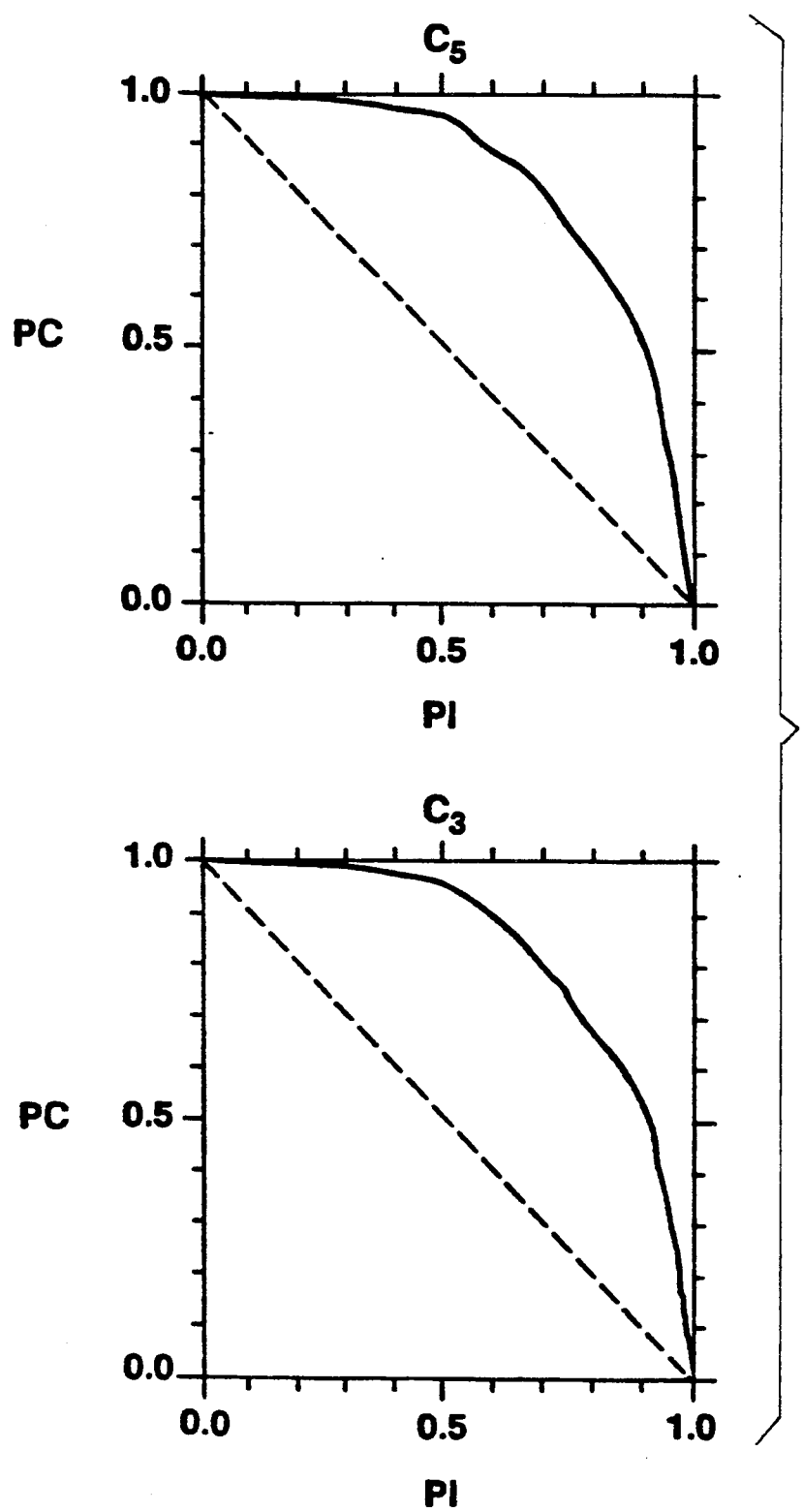
Figure 21:
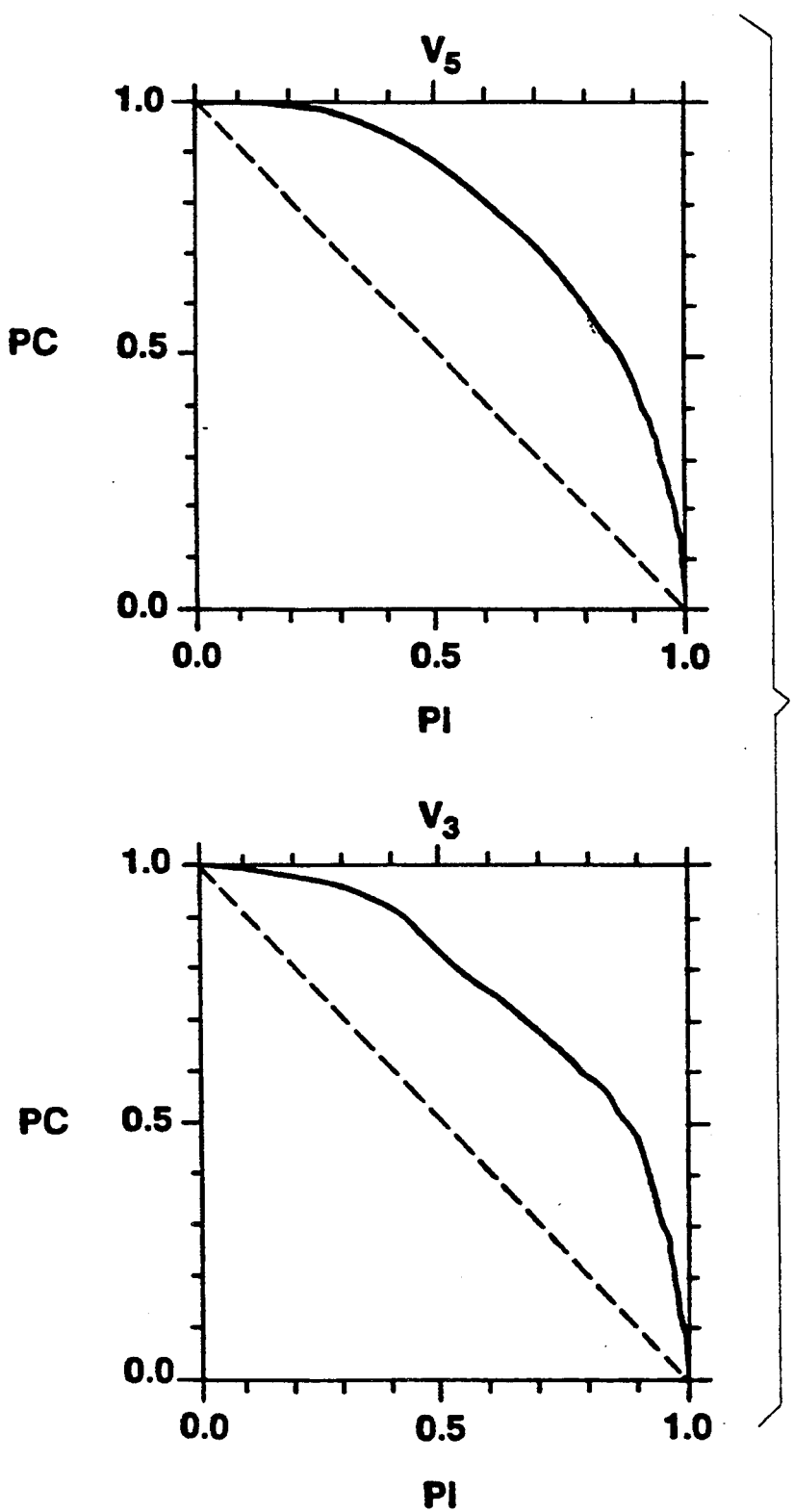
Figure 22:
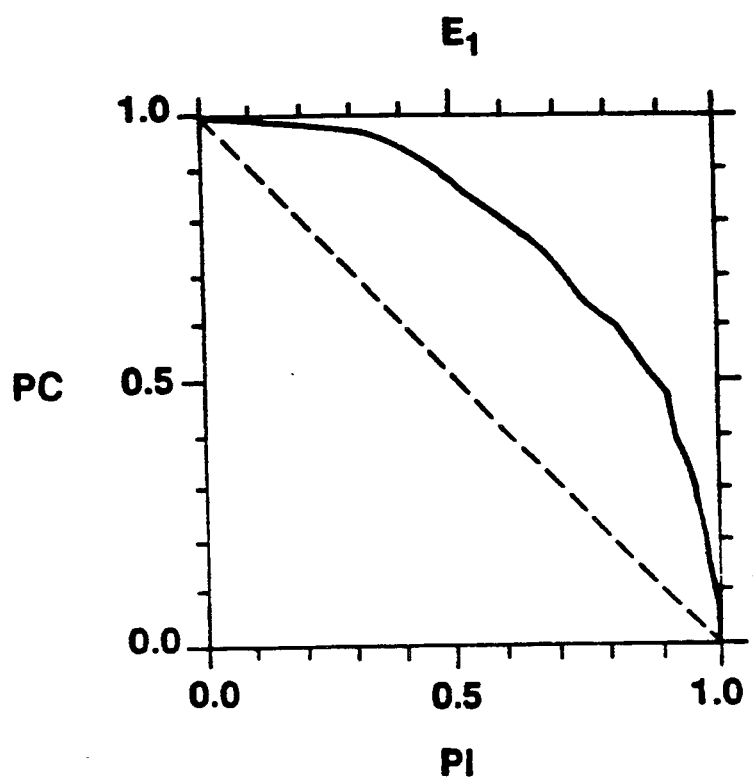

FIG. 14 is a chart illustrating the steps to be followed in generating the required histograms. In Step A, a population of ECG signals is obtained, from either epicardial or body surface sensor arrays. In Step B, based on physiological observations, the signals are classified as either normal or ischemic. In Step C, for each decision variable ischemia (I) and control (C) histograms are plotted. This is done only if the amount of data classified into normal and ischemic categories in Step B is sufficient to guarantee statistical significance. By way of example, histograms for the decision variables $f_0$, $w_0$ and $e_0$ are shown in FIGS. 15(a), 15(b) and 15(c), respectively, where "I" indicates ischemia, "C" indicates control and "T" indicates the threshold value. Finally, in Step D, the receiver operating characteristics (ROC) for each one of the decision variables are computed and plotted. These are shown in the $P_I$ v. $P_C$ graphs of FIGS. 16–22. This enables proper selection of the threshold value and comparison of the performance of the various detection schemes.

If desired, a multivariate histogram could be generated in Step E. All decision variables would be combined together into a single multivariate probability density function for control, and another probability density function for ischemia. This would be a straightforward exercise which need not be described in detail herein.

Figure 23A:
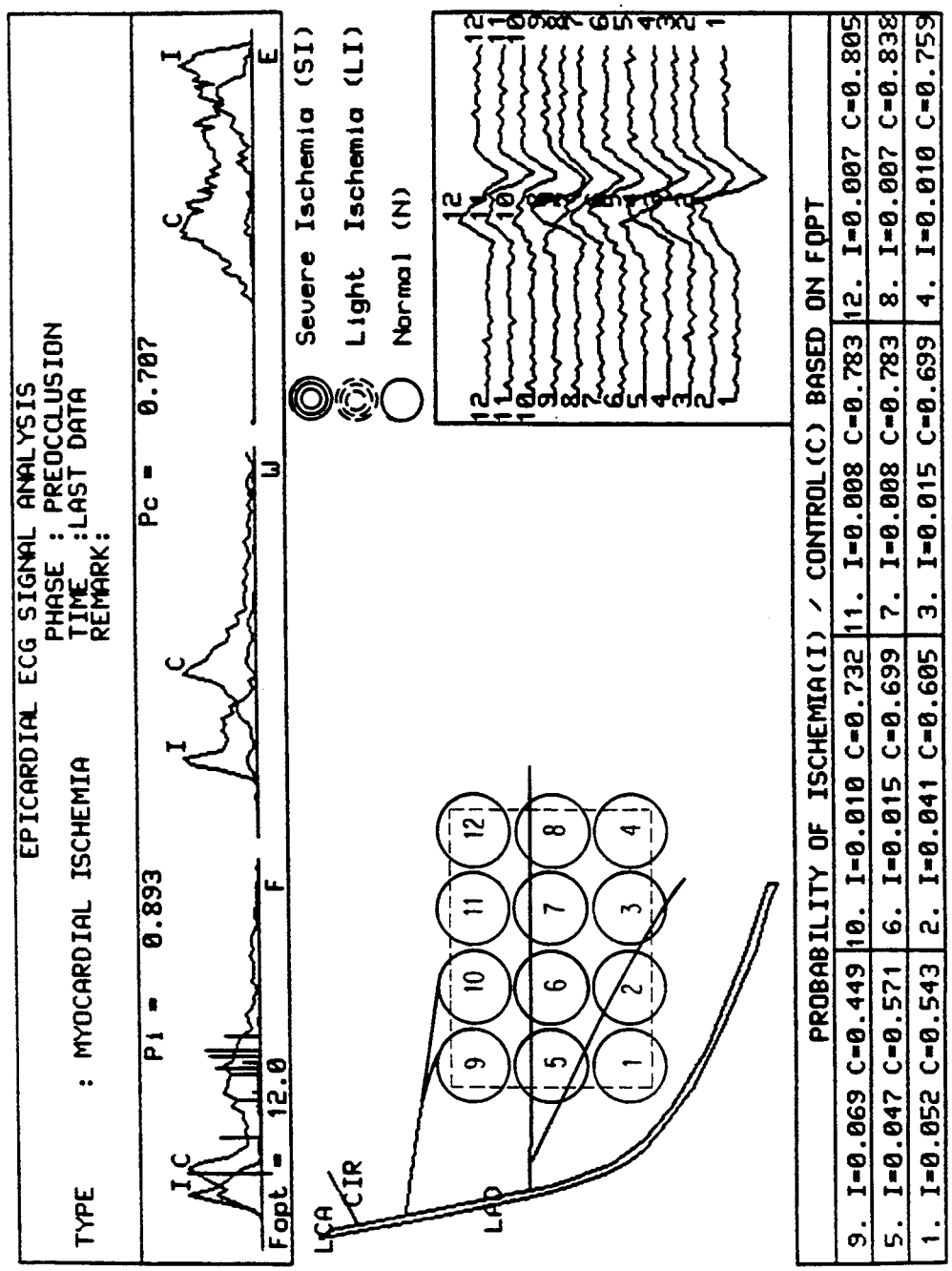

An example of the use of the $f_0$, $w_0$ and $e_0$ decision variables in quantifying and localizing an area of myocardial ischemia is shown in FIGS. 23 and 24. FIG. 23(a) shows the histograms of the $f_0$, $w_0$ and $e_0$ decision variables, with the location of the threshold T and specific ECG array points shown as they relate to one another, and the anatomy of the LAD and Circumflex-CA with the ECG sensor locations and the sites of occlusion of the LAD branches (designated by the x's). Also shown in FIG. 23(a) are the digitized primary ECG signals from each array sensor which were used to obtain the decision variables. In FIG. 23(a), all branches of the left anterior coronary artery are open.

Figure 23B:
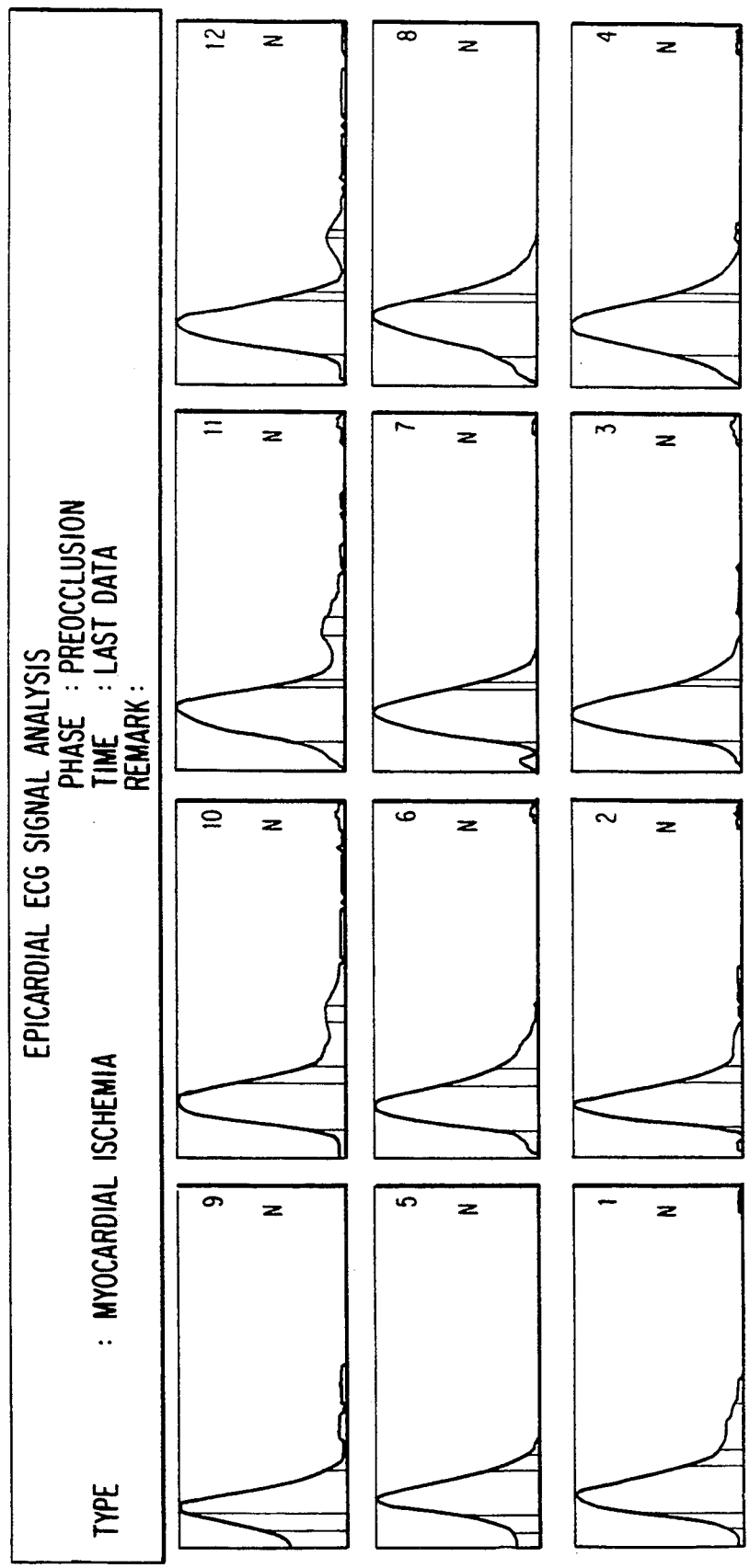

FIG. 23(b) shows the histograms of the signals from each of the 12 sensors together with the probability diagnosis of ischemia (I) or control (C) based on the $f_0$ decision variable. FIG. 23(c) sets forth the optimum decision variables $e_{OPT}$, $w_{OPT}$ and $f_{OPT}$ for each of the histograms.

Figure 24A:
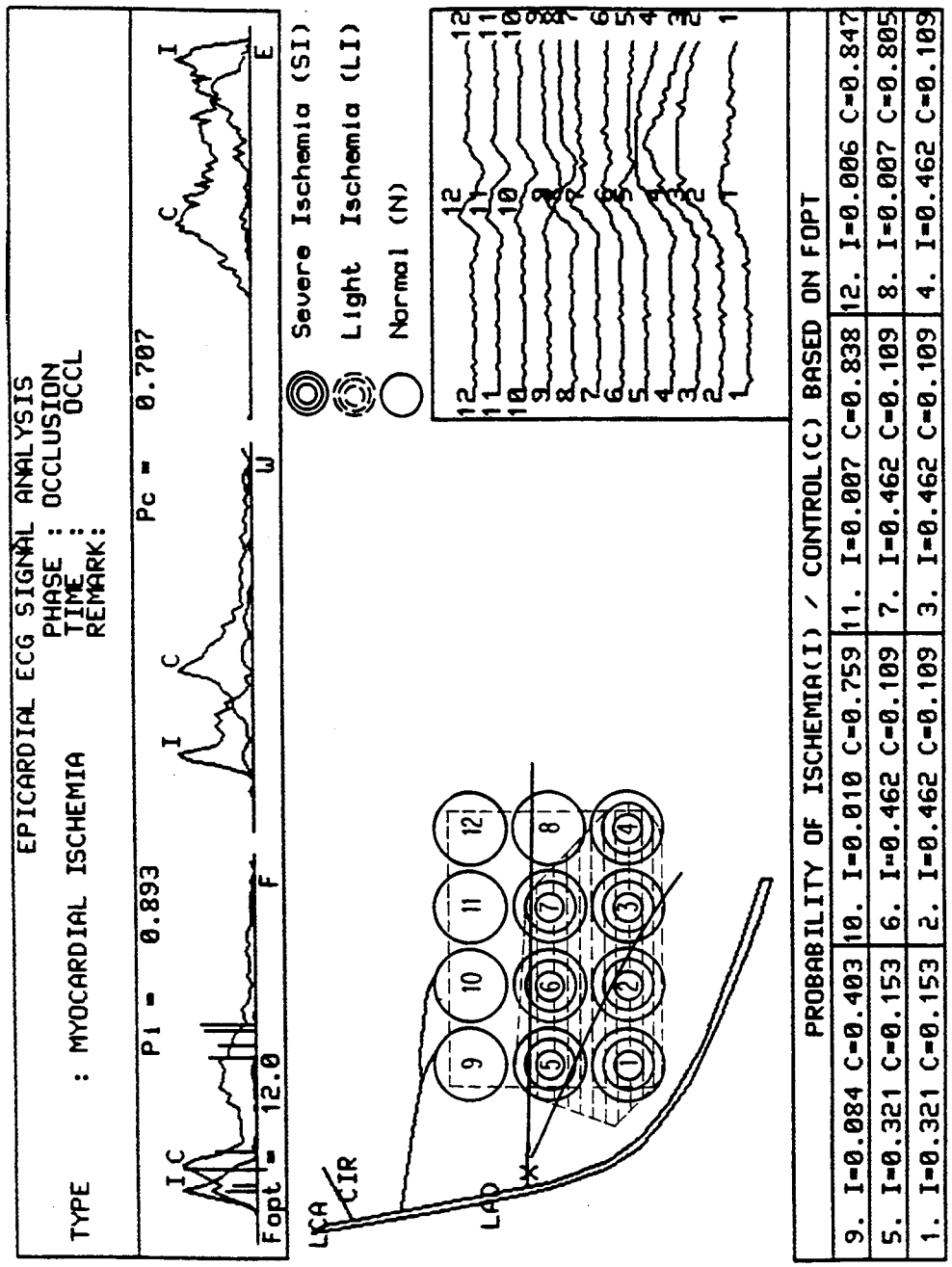
Figure 24B:
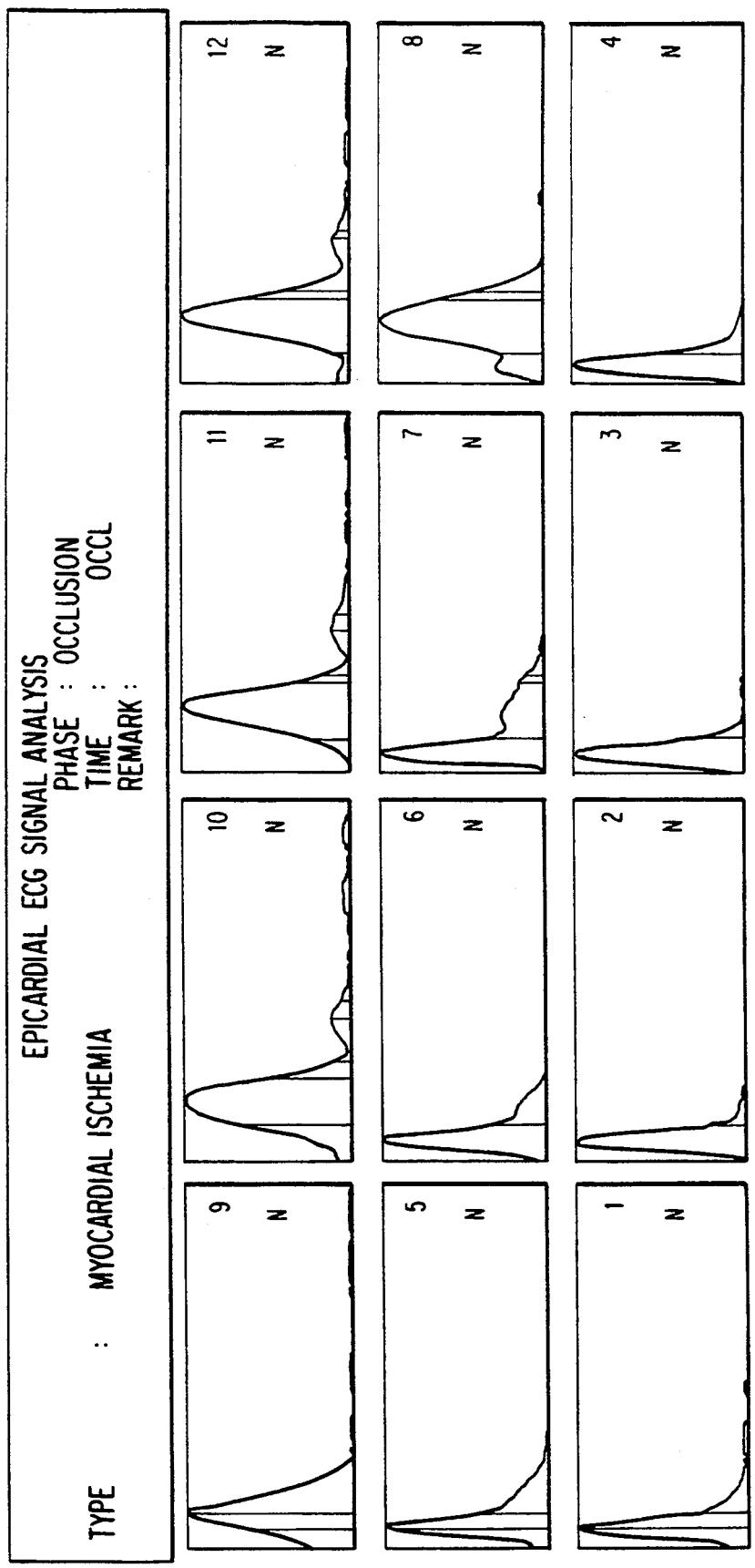

FIGS. 24(a)–24(c) illustrate the same data after 15 minutes of occlusion of the second diagonal LAD branch. FIG. 24(b) shows the probability diagnosis of severe ischemia (SI) or normal (N) control based on the probability of ischemia v. control for each point. Note reduction of $f_{OPT}$ ($f_0$) and $w_{OPT}$ ($w_0$) decision variables and the increase in $e_{OPT}$ ($e_0$) decision variable. The probability of ischemia based on the $f_0$ decision variable is shown in the probability density function histogram for $f_0$, and the threshold value for ischemia using $f_{OPT}$ = 12.0 Hz is also shown, as are the specific probabilities of ischemia and control for each ECG sensor.

A suitable method for obtaining information on both the existence and degree of ischemia may be as follows. With the probability of ischemia and probability of control for each being obtained from the probability density function histogram for the $f_0$ decision variable as indicated above, and with the specific probabilities for each sensor are designated I for the probability of ischemia and C for the probability of control or normal, then the probabilities I and C can be subjected to a quantitative decision-making process to assign areas as either ischemic or normal while also obtaining information as the degree of ischemia. An example of a suitable quantitative decision-making algorithm would be as follows:

1. IF I≦QV AND C≦QV, then Light Ischemia.
2. IF I>QV, THEN ischemia.
3. IF C>QV, THEN control, or normal.

where QV is a quantification value chosen by optimizing the probability criteria. For canines, a typical example may be 0.3, depending on how conservative one wishes to be in the diagnosis. Other evaluation schemes could also be used, and this is but one illustrative example. In the above example, the specific probabilities I and C derived for each sensor may be referred to as a "quantification probability" or "quantification index" providing a measure of the probability of ischemia or control. In the broader context of muscular dysfunction, this may be referred to as a "muscular dysfunction quantification index", and in the particular context of myocardial ischemia this would be referred to as a "myocardial ischemia quantification index." The myocardial ischemia quantification index may then be subjected to a quantitative decision-making algorithm to differentiate between normal, light ischemia and ischemia.

Figure 25:
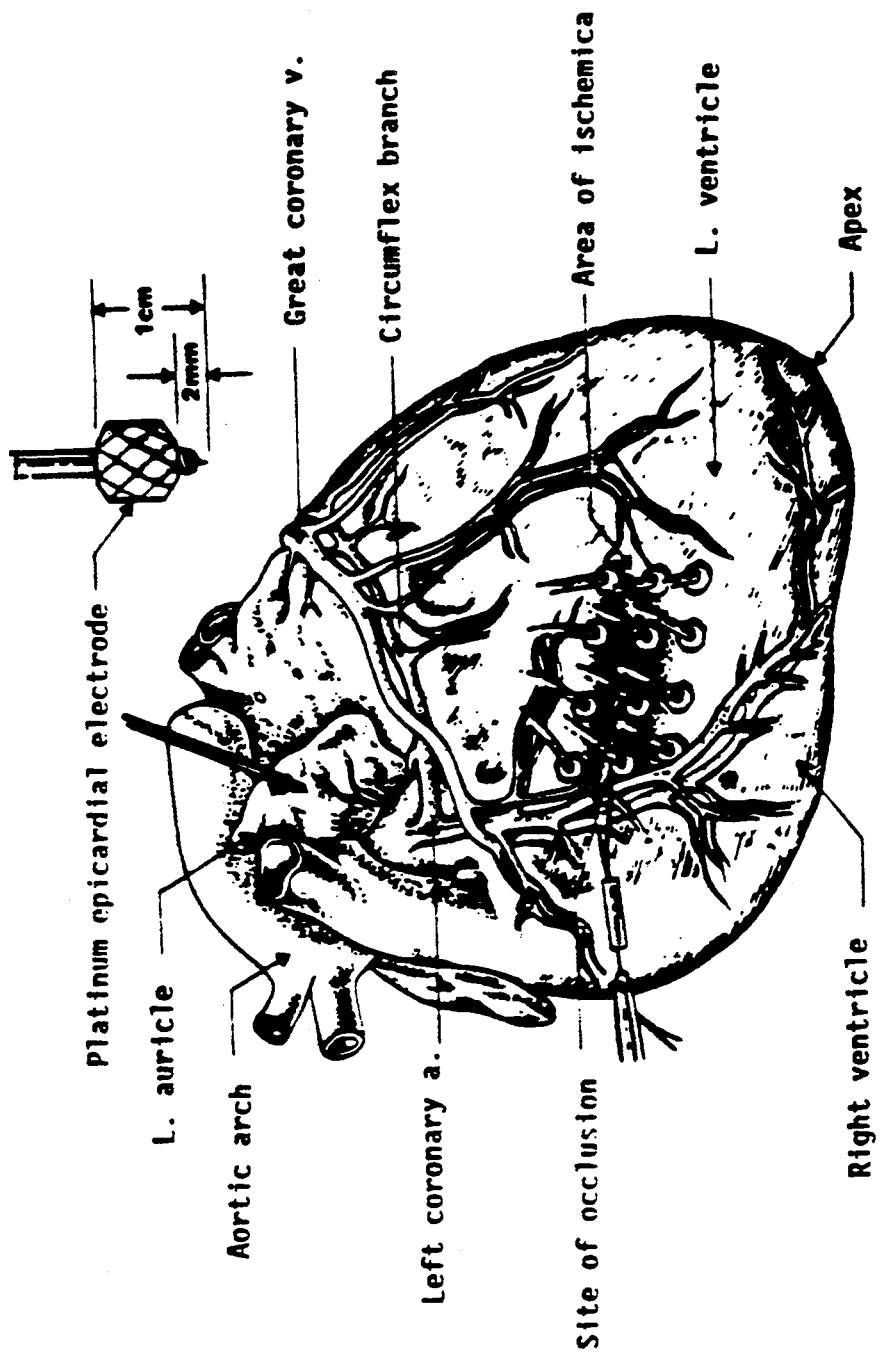
FIG. 25 is an illustration of experimental preparation for epicardial ECG studies using an ECG sensor array distributed about the second diagonal branch of the left anterior descending (LAD) coronary artery, with a ligature placed about the proximal LAD second diagonal for creation of reversible localized area of low flow ischemia.

Epicardial ECG studies validating the results achieved by the present invention were carried out on an intact canine heart model in which an array of 12 epicardial ECG sensors were placed on the left ventricular surface of the heart about the 2nd, or 2nd and 3rd, diagonal branches of the left anterior descending (LAD) coronary artery, as shown in FIG. 25. A snare ligature was placed about the 2nd (or 2nd and 3rd) coronary diagonal LAD, so that this vessel could be occluded without reducing flow through the main LAD. Thus, a reversible localized area of ischemic low flow myocardium could be created, surrounded by normally perfused heart muscle supplied by the other LAD branches. Flow into the ischemic area was supplied by the generous collateral anastomotic connections which are present in the normal canine heart and this animal model was specifically chosen to insure ischemia rather than infarction in the areas of LAD branch occlusion. The electrode array was placed so as to include both the normally perfused, ischemic and border zone ischemic myocardium. The electrodes were placed at 1 or 1.5 cm±0.1 cm intervals (depending on heart size and anatomy) in a regular rectangular pattern as a grid array of 4×3 or 3×4 sensors.

Platinum "corkscrew" electrodes (FIG. 25) were used to simultaneously record electrical activity on the epicardial surface of the left ventricular wall. The electrode signals were routed to 12 channels of ECG amplifiers of minimum input impedance of 500 kohms, bandwidth 0.5–250 Hz, and with CMRR of 80 dB or higher. Monopolar ECG signals were referenced to a standard Wilson Central Terminal. The amplified signals were sampled by a 12-channel analog to digital (A/D) converter system (LPS) and recorded digitally on a DEC PDP 11/45 computer. Each data set consisted of 500 samples from each of the 12 electrodes, with 2 ms sampling period.

After placement of the epicardial electrodes with the snare ligature in the open position, a one hour period of equilibration was permitted before ECG array observations were made. Then the control ECG signals were obtained. To produce acute ischemia, the snare ligature was tightened, stopping arterial inflow, though allowing collateral flow to the ischemic region of myocardium. The magnitude of the ischemic response was monitored serially at the experimental control terminal.

In FIGS. 15(a)–15(c) are shown the histograms of the estimated probability density functions (PDF$_S$) under control (C) and ischemic (I) conditions for the peak frequency optimum $f_0$, frequency width optimum $w_0$ and autocorrelation eigenvalue difference optimum ($e_0$) decision variables. In each decision variable histogram set ($f_0,w_0,e_0$), a threshold value (T in FIGS. 15(a)–15(c) for $\gamma$ has been chosen which defines the probabilities of ischemia ($P_I$) and of control ($P_C$) at which the Neyman-Pearson (NP) test is to be applied to establish the specific probabilities (I) and (C) of each data point obtained from a given animal's epicardial ECG array. The detection level defined by the threshold (T) level of $\gamma$ implies the probability of having detected an ischemic ECG channel when it is truly ischemic and the probability of having detected control when it is control. As is clear from the histograms, as T is shifted to lower values of $f_0$ and $w_0$, and higher values of $e_0$, the probability $P_I$ of correctly predicting ischemia becomes closer to 1.0, but the probability $P_C$ of correctly predicting normal conditions falls. Thus, one may overpredict ischemia and underpredict normality. Ultimately, the value of the threshold is determined by the physcian and depends on how conservative one wishes to be in interpreting the criteria of ischemia. In these experiments, as will be discussed later, an optimal threshold value for each decision variable ($f_0,w_0,e_0$) was chosen both on their histogram location of T, as well as on the basis of how well this threshold could explain the biochemical evidence of ischemia.

One illustrative example of the test results is shown in FIG. 24. In FIGS. 24(a)–24(c), the $f_0$ decision variable was set at a threshold value for $\gamma$ of 12.0 Hz which produces a $P_I$= 0.893 and a $P_C$=0.707. In this case, the signal processing delineation of severe ischemia (SI) from $f_0$ corresponds exactly with the cyanotic area of myocardium shown by the shaded area in the anatomic figure. The individual sensor frequency histograms for ECG sensors 1–7 show a reduction in peak $f_0$ below 9.8 Hz, compared to the normal areas where the $f_0$ is >21 Hz, and the probability of ischemia in these SI areas rises to I>0.321 while C falls to less than 0.103. Similar ischemic changes are seen in $w_0$ and $e_0$ for these areas.

Because the various decision variables measure different aspects of the ECG signal, they may be more or less sensitive in defining border zone or Light ischemic areas. Thus, various decision variables may reinforce each other and may allow better, and more subtle discrimination of ischemia levels.

Figure 26:
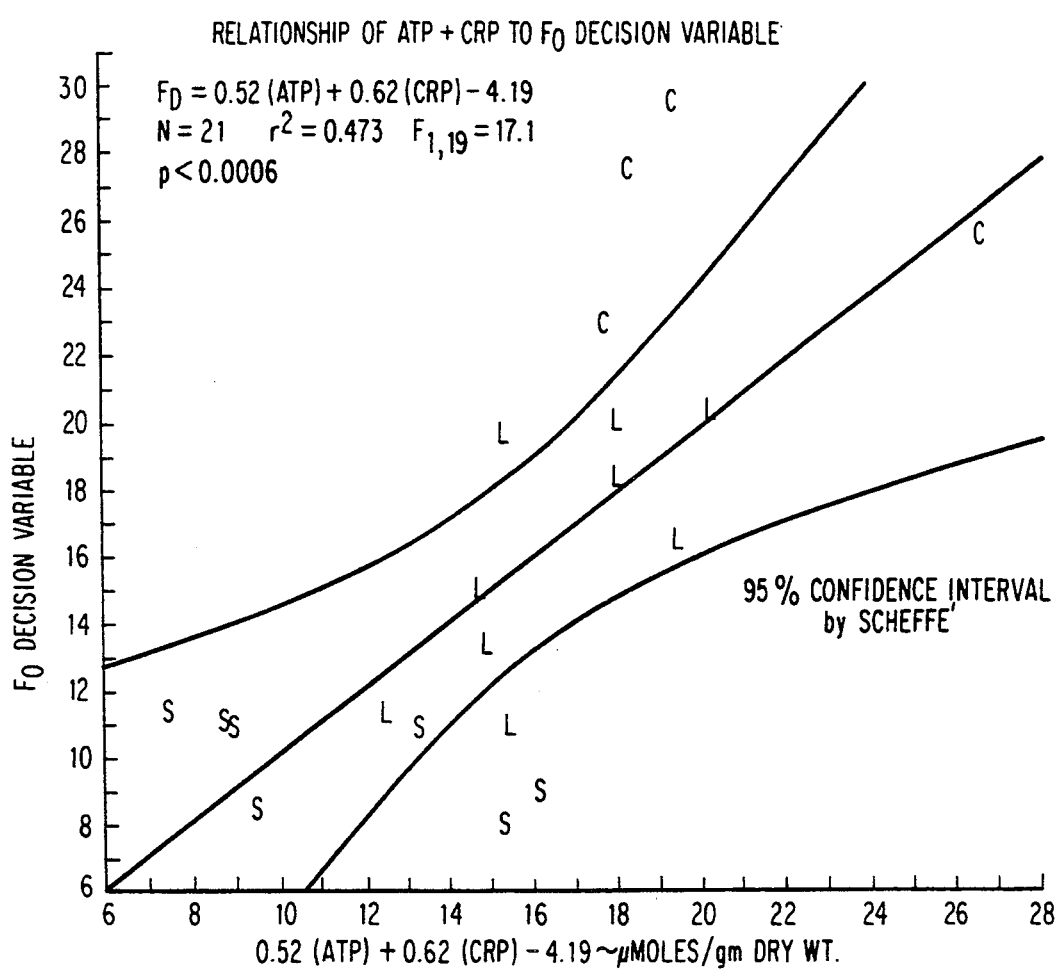
FIG. 26 is a plot showing the mean regression line and 95% confidence interval (by Scheffe' analysis of all contrasts) for the $f_0$ to ATP+CRP relationship.

Tests have shown that the alterations in the ECG Signal Processing ($f_0,w_0,e_0$), which occur decision variables in reversible myocardial ischemia and reflect changes in the activation of the myocardium, are a quantitative reflection of the underlying myocardial biochemical changes, and that the parameters are very sensitive to early ischemic modification of myocardial energetics and glucose oxidation. In particular the spectrum domain decision variables appear to reflect the sum of ATP plus CRP, thus quantifying cardiac high energy phosphates and the rising level of myocardial tissue lactate (See, for example, T. C. Vary, D. K. Reibel and J. R. Neely, Control of Energy Metabolism of Heart Muscle, Ann. Rev. Physiol., vol. 43, pp. 419–430, 1981). Finally, while myocardial creatine phosphate (CRP) tends to be protected during Light or early ischemia, there are falls in ATP and both ATP and CRP fall in severe ischemia. These data suggest, but do not prove, that while myofibrillar high energy phosphates (CRP) are protected during partial ischemia that other ATP sources perhaps associated with the mitochondria or the cell membrane are depleted early as the ischemic changes in activation occur. Late in the ischemic process, but still in the potentially reversible phase, described by (Reference 14), total high energy reserves are depleted in an attempt to maintain ATP levels, since CRP falls but ATP levels remain unchanged between LI and SI. However, the sum of ATP plus CRP falls as a continuous variable providing a quantification of the severity of myocardial ischemia which can in turn be quantified by the $f_0,w_0$ and $e_0$ decision variables. This can be seen, for example, in FIG. 26 which shows the mean regression line and 95% confidence interval (by Scheffe' analysis of all contrasts) for the $f_0$ to ATP+CRP relationship. Although the sum of ATP plus CRP only explains 47% of the variability ($r^2$=0.473) in $f_0$, the relation is highly significant ($p<0.0006$) and demonstrates the $f_0$ is truly a continuous decision variable which is a direct reflection of the myocardial energetic level. When $e_0$ was added to $f_0$ the explained variability was increased to 48% ($p. < 0.003$). Similar results were found using the other decision variables. For a more detailed discussion of the experimental validation of the techniques of this invention, reference may be had to J. H. Siegel and C. L. Nikias, Advance Signal Processing Methodology For the Detection, Localization and Quantification of Acute Myocardial Ischemia, Surgery (in press 1987).

The importance of these studies using advanced signal processing methodologies to transform the time domain ECG signal into the frequency spectrum and autocorrelation domains is that for the first time they develop a set of quantifiable parameters of ischemic abnormalities in ECG activation which can be treated as events with probabilistic determination. This approach using the special case of the general Bayes criteria, the minimum error probability (min-max or Neyman-Pearson Test) provides an objective quantification of any new ECG data based on the histogram of past experiences without any a priori assumptions. While it is still necessary to choose a threshold level of the decision variable (or combination of variables) to apply the test for minimization of error, this too can be independently verified by comparing the decision variable threshold to the levels of the biochemical parameters of ischemia.

The present invention would be useful in intraoperative quantification of myocardial ischemia and the probabilistic evaluation of the likely success of coronary revascularization procedures by direct measurement of regional cardiac epicardial or transmural activation potentials. It may also find utility in the endocardial localization of ischemic areas of the ventricle which may be responsible for inducible ventricular arrhythmias at the time of intracavitary Programmed Electrical Stimulation (PES). Finally, it may be possible to apply this type of ECG signal transformation and probabilistic decision-making to the localization of epicardial projections of areas of myocardial ischemia by non-invasive methods using a practical limited inverse model of electrocardiography for the interpretation of torso array signals.

Finally, while the present invention has been described in the context of the detection of myocardial ischemia, it will be appreciated that the technique itself involves the evaluation of unipolar signals representing muscle activation, and that the invention may also be applicable to detecting other muscle dysfunctions.

What is claimed is:

1. A method of detecting myocardial ischemia from a time-domain ECG signal $X(n)$; $n=0,1,\ldots,N$, where N is an integer, comprising the steps of:
   providing an ECG sensor;
   detecting said ECG signal from said ECG sensor;
   generating a decision variable from said ECG signal;
   comparing said decision variable to a histogram of previously obtained sensor signal data to obtain a myocardial ischemia quantification index corresponding to a probability of ischemia; and
   comparing said quantification index to a selected value to determine the presence of myocardial ischemia.

2. A method as defined in claim 1, wherein said generating step comprises converting said ECG signal to the spectrum domain and determining the peak frequency of the converted signal as said variable.

3. A method of detecting myocardial ischemia from a time-domain ECG signal $X(n)$; $n=0,1,\ldots,N$, where N is an integer, comprising the steps of:
   providing an ECG sensor;
   detecting said ECG signal from said ECG sensor;
   generating a plurality of decision variables from said ECG signal;
   comparing said decision variables to at least one histogram of previously obtained sensor signal data to obtain at least one myocardial ischemia quantification index corresponding to a quantification probability of ischemia based on said comparison results; and
   comparing said quantification index to a selected value to determine the presence of myocardial ischemia.

4. A method of detecting the existence of muscle dysfunction from a unipolar signal $X(n)$; $n=0,1\ldots,N$, representing activation of said muscle, where N is an integer, said method comprising the steps of:
   providing an ECG sensor;
   detecting said unipolar signal from said muscle activation signal sensor;
   generating a decision variable from said unipolar signal;
   comparing said decision variable to a threshold value of said decision variable to obtain a muscular dysfunction quantification index corresponding to a quantification probability of the existence of muscle dysfunction; and
   comparing said quantification index to a selected value to determine the presence of muscle dysfunction.

5. A method as defined in claim 4, further comprising determining a degree of said dysfunction based on the comparison of said quantification index to said value.

6. A method as defined in claim 5, wherein said muscle dysfunction is myocardial ischemia.

7. A method as defined in claim 4, wherein said muscle dysfunction is myocardial ischemia.

8. A method as defined in claim 7, wherein said histogram has a non-Gaussian distribution.

9. A method of detecting myocardial ischemia from a time-domain ECG signal $X(n)$; $n=0,1,\ldots,N$, where N is an integer, comprising the steps of:
   providing an ECG sensor;
   detecting said ECG signal from an ECG sensor;
   generating a decision variable from said ECG signal;
   generating a histogram from a plurality of preliminary ECG signals corresponding to both normal and ischemic conditions;
   comparing said decision variable to said histogram to obtain a myocardial ischemia quantification index corresponding to a quantification probability of ischemia; and
   comparing said quantification index to a selected value to determine the presence of myocardial ischemia.

10. A method of detecting the existence of muscle dysfunction from a unipolar signal $X(n)$; $n=0,1,\ldots,N$, representing activation of said muscle, where N is an integer, said method comprising the steps of:
    providing an ECG sensor;
    detecting said unipolar signal from said muscle activation sensor;
    generating a histogram from a plurality of preliminary unipolar signals corresponding to both normal and dysfunctional conditions;

generating a decision variable from said unipolar signal;

comparing said decision variable to said histogram to obtain a muscular dysfunction quantification index corresponding to a quantification probability of the existence of muscular dysfunction; and comparing said quantification index to a selected value to determine the existence of muscle dysfunction.

11. A method of detecting myocardial ischemia from a time-domain ECG signal $X(n)$; $n=0,1,\ldots,N$, where N is an integer, comprising the steps of:

providing an ECG sensor;

detecting said ECG signal from an ECG sensor;

generating a decision variable from said ECG signal;

selecting a threshold value for said decision variable corresponding to a probability of correctly detecting myocardial ischemia when myocardial ischemia is present;

comparing said decision variable to said threshold value of said decision variable to obtain comparison results; and determining a myocardial ischemia quantification index corresponding to a quantification probability of ischemia based on said comparison results.

12. A method as defined in claim 11, wherein said step of selecting a threshold value comprises selecting said threshold value in accordance with a histogram of previous values of said decision variable.

13. A method of detecting myocardial ischemia from a time-domain ECG signal $X(n)$; $n=0,1,\ldots,N$, where N is an integer, comprising the steps of:

providing an ECG sensor;

detecting said ECG signal from said ECG sensor;

generating a plurality of decision variables from said ECG signal;

combining said decision variables to form a combined decision variable in a multivariate probability space;

comparing said combined decision variable to a histogram of a plurality of combined decision variables generated from previously obtained sensor signal data to obtain a myocardial ischemia quantification index corresponding to a quantification probability of ischemia; and comparing said quantification index to a selected value to determine the existence of myocardial ischemia.

14. A method of detecting the existence of muscle dysfunction from a unipolar signal $X(n)$; $n=0,1,\ldots,N$, representing activation of said muscle, where N is an integer, said method comprising the steps of:

providing a muscle activation signal sensor;

detecting said unipolar signal from said muscle activation sensor;

generating a decision variable from said unipolar signal;

selecting a threshold value for said decision variable corresponding to a probability of correctly detecting myocardial ischemia when myocardial ischemia is present;

comparing said decision variable to said threshold value of said decision variable to obtain comparison results; and determining a muscular dysfunction quantification index corresponding to a quantification probability of the existence of muscle dysfunction based on said comparison results.

* * * * *